United States Patent
Malkowski

(10) Patent No.: US 10,537,329 B2
(45) Date of Patent: *Jan. 21, 2020

(54) SURGICAL CLIP APPLIER

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 15/665,820

(22) Filed: Aug. 1, 2017

(65) Prior Publication Data
US 2017/0325814 A1  Nov. 16, 2017

Related U.S. Application Data

(63) Continuation of application No. 14/146,126, filed on Jan. 2, 2014, now Pat. No. 9,750,500.

(60) Provisional application No. 61/754,143, filed on Jan. 18, 2013.

(51) Int. Cl.
*A61B 17/10* (2006.01)
*A61B 17/128* (2006.01)
*A61B 17/08* (2006.01)

(52) U.S. Cl.
CPC .......... *A61B 17/105* (2013.01); *A61B 17/083* (2013.01); *A61B 17/1285* (2013.01)

(58) Field of Classification Search
CPC . A61B 17/105; A61B 17/083; A61B 17/1285; A61B 17/068
See application file for complete search history.

(56) References Cited

U.S. PATENT DOCUMENTS

| 3,120,230 A | 2/1964 | Skold |
| 3,363,628 A | 1/1968 | Wood |
| 3,638,847 A | 2/1972 | Noiles et al. |
| 3,867,944 A | 2/1975 | Samuels |
| 4,242,902 A | 1/1981 | Green |

(Continued)

FOREIGN PATENT DOCUMENTS

| AU | 2010200641 A1 | 10/2010 |
| AU | 2013254887 A1 | 11/2013 |

(Continued)

OTHER PUBLICATIONS

European Office Action corresponding to European Appln. No. EP 16 15 9324.9 dated Aug. 7, 2017.

(Continued)

*Primary Examiner* — Richard G Louis

(57) ABSTRACT

A surgical clip applier is provided including a housing, at least one handle pivotably connected to the housing, a channel assembly extending distally from the housing, a clip carrier disposed within said channel assembly and defining a channel therein, a plurality of clips slidably disposed within the channel of said clip carrier, a jaw assembly including a pair of jaws extending from an end of the channel assembly, opposite the housing, adapted to accommodate a clip therein and being operable to effect formation of a clip in response to movement of said at least one handle, and a shuttle bar slidably supported in the channel assembly and configured to transport a clip from the clip carrier to the jaw assembly.

19 Claims, 32 Drawing Sheets

(56) References Cited

U.S. PATENT DOCUMENTS

| | | |
|---|---|---|
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,430,997 A | 2/1984 | DiGiovanni et al. |
| 4,449,531 A | 5/1984 | Cerwin et al. |
| 4,471,780 A | 9/1984 | Menges et al. |
| 4,478,220 A | 10/1984 | Di Giovanni et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,592,498 A | 6/1986 | Braun et al. |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,951,860 A | 8/1990 | Peters et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,418 A | 3/1992 | Yoon et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |

(56) References Cited

U.S. PATENT DOCUMENTS

| | | |
|---|---|---|
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,445,167 A | 8/1995 | Yoon et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Vleade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |

(56) References Cited

U.S. PATENT DOCUMENTS

| | | |
|---|---|---|
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,952,060 B2 | 5/2011 | Watanabe et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,145 B2 | 4/2012 | Shelton, IV et al. |

(56) References Cited

U.S. PATENT DOCUMENTS

| | | |
|---|---|---|
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,915,930 B2 | 12/2014 | Huitema et al. |
| 8,920,438 B2 | 12/2014 | Aranyi et al. |
| 8,939,974 B2 | 1/2015 | Boudreaux et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,973,804 B2 | 3/2015 | Hess et al. |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,282,961 B2 | 3/2016 | Whitman et al. |
| 9,326,776 B2 | 5/2016 | Gadberry et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,480,477 B2 | 11/2016 | Aranyi et al. |
| 9,498,227 B2 | 11/2016 | Zergiebel et al. |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 * | 9/2017 | Malkowski .......... A61B 17/083 |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |

(56) References Cited

U.S. PATENT DOCUMENTS

| | | |
|---|---|---|
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |

(56) References Cited

U.S. PATENT DOCUMENTS

| | | |
|---|---|---|
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0188872 A1 | 8/2008 | Duff |
| 2008/0228199 A1 | 9/2008 | Cropper et al. |
| 2008/0243145 A1 | 10/2008 | Whitfield et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0264904 A1 | 10/2009 | Aldrich et al. |
| 2009/0326558 A1 | 12/2009 | Cui et al. |
| 2010/0049216 A1 | 2/2010 | Zergiebel |
| 2010/0057105 A1 | 3/2010 | Sorrentino et al. |
| 2010/0057107 A1 | 3/2010 | Sorrentino et al. |
| 2010/0274254 A1 | 10/2010 | Boileau et al. |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087242 A1 | 4/2011 | Pribanic et al. |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0295290 A1 | 12/2011 | Whitfield |
| 2011/0313437 A1 | 12/2011 | Yeh |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0123446 A1 | 5/2012 | Aranyi et al. |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0310259 A1 | 12/2012 | Sorrentino et al. |
| 2012/0330326 A1 | 12/2012 | Creston et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0175320 A1 | 7/2013 | Mandakolathur Vasudevan et al. |
| 2013/0190779 A1 | 7/2013 | Whitfield et al. |
| 2013/0190780 A1 | 7/2013 | Whitfield et al. |
| 2013/0226200 A1 | 8/2013 | Kappel et al. |
| 2013/0253540 A1 | 9/2013 | Castro et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2014/0005693 A1 | 1/2014 | Shelton, IV et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0074143 A1 | 3/2014 | Fitzgerald et al. |
| 2014/0194903 A1 | 7/2014 | Malkowski et al. |
| 2014/0263565 A1 | 9/2014 | Lytle, IV et al. |
| 2014/0276970 A1 | 9/2014 | Messerly et al. |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |

(56) References Cited

U.S. PATENT DOCUMENTS

| | | | |
|---|---|---|---|
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CA | 1163889 A | 3/1984 |
| CA | 2740831 A1 | 4/2010 |
| CN | 1994236 A | 7/2007 |
| CN | 101401737 A | 4/2009 |
| CN | 101530340 A | 9/2009 |
| CN | 100571640 C | 12/2009 |
| CN | 101658437 A | 3/2010 |
| CN | 101664329 A | 3/2010 |
| CN | 101664331 A | 3/2010 |
| CN | 201683954 U | 12/2010 |
| CN | 103083059 A | 5/2013 |
| CN | 103181809 A | 7/2013 |
| CN | 103181810 A | 7/2013 |
| CN | 104487006 A | 4/2015 |
| CN | 104605911 B | 2/2017 |
| DE | 202007003398 U1 | 6/2007 |
| DE | 20 2009 006113 U1 | 7/2009 |
| EA | 0086721 A2 | 8/1983 |
| EP | 0073655 A1 | 3/1983 |
| EP | 0085931 A2 | 8/1983 |
| EP | 0089737 A1 | 9/1983 |
| EP | 0092300 A1 | 10/1983 |
| EP | 0324166 A2 | 7/1989 |
| EP | 0392750 A1 | 10/1990 |
| EP | 0409569 A1 | 1/1991 |
| EP | 0569223 A1 | 11/1993 |
| EP | 0598529 A2 | 5/1994 |
| EP | 0622049 A1 | 11/1994 |
| EP | 0685204 A1 | 12/1995 |
| EP | 0732078 A2 | 9/1996 |
| EP | 0755655 A2 | 1/1997 |
| EP | 0760230 A1 | 3/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1468653 A2 | 10/2004 |
| EP | 1609427 A1 | 12/2005 |
| EP | 1712187 A2 | 10/2006 |
| EP | 1712191 A2 | 10/2006 |
| EP | 1757236 A2 | 2/2007 |
| EP | 1813199 A1 | 8/2007 |
| EP | 1813207 A1 | 8/2007 |
| EP | 1894531 A2 | 3/2008 |
| EP | 1908423 A2 | 4/2008 |
| EP | 1913881 A1 | 4/2008 |
| EP | 1939231 A1 | 7/2008 |
| EP | 2000102 A2 | 12/2008 |
| EP | 2140817 A1 | 1/2010 |
| EP | 2229895 A1 | 9/2010 |
| EP | 2 263 570 A1 | 12/2010 |
| EP | 2332471 A1 | 6/2011 |
| EP | 2412318 A2 | 2/2012 |
| EP | 2412319 A2 | 2/2012 |
| EP | 2 752 165 A2 | 7/2014 |
| GB | 1134832 A | 11/1968 |
| GB | 2073022 A | 10/1981 |
| GB | 2 132 899 A | 7/1984 |
| JP | 10118083 | 5/1998 |
| JP | 2003033361 A | 2/2003 |
| JP | 2006501954 A | 1/2006 |
| JP | 2006154230 A | 6/2006 |
| JP | 2006209948 A | 8/2006 |
| JP | 2006277221 A | 10/2006 |
| JP | 2007250843 A | 9/2007 |
| JP | 2008017876 A | 1/2008 |
| JP | 2008047498 A | 2/2008 |
| JP | 2008055165 A | 3/2008 |
| JP | 2008515550 A | 5/2008 |
| JP | 2009198991 A | 9/2009 |
| JP | 5499386 B2 | 5/2014 |
| WO | 0042922 A1 | 7/2000 |
| WO | 01/65997 A2 | 9/2001 |
| WO | 2001-66001 A2 | 9/2001 |
| WO | 2001-67965 A1 | 9/2001 |
| WO | 2003-086207 A1 | 10/2003 |
| WO | 2003-092473 A2 | 11/2003 |
| WO | 2004032762 A1 | 4/2004 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Chinese First Office Action corresponding to Chinese Appln. No. CN 2014104295806 dated Aug. 31, 2017.

Extended European Search Report corresponding to European Appln. No. EP 17 17 3508.7 dated Sep. 29, 2017.

Extended European Search Report corresponding to European Appln. No. EP 17 18 0570.8 dated Dec. 6, 2017.

Extended European Search Report corresponding to Patent Application EP 18154617.7 dated Jun. 25, 2018.

Extended European Search Report corresponding to Patent Application EP 18155158.1 dated Jun. 28, 2018.

European Search Report corresponding to Patent Application EP 15877428.1 dated Jul. 2, 2018.

European Search Report corresponding to Patent Application EP 18157789.1 dated Jul. 5, 2018.

Canadian Office Action corresponding to Patent Application CA 2,972,444 dated Aug. 9, 2018.

European Search Report corresponding to Patent Application EP 18156458.4 dated Sep. 3, 2018.

European Search Report corresponding to Patent Application EP 18171682.0 dated Sep. 18, 2018.

European Search Report corresponding to Patent Application EP 15878354.8 dated Sep. 19, 2018.

European Search Report corresponding to Patent Application EP 18183394.8 dated Sep. 28, 2018.

Extended European Search Report corresponding to Patent Application EP 18163041.9 dated Sep. 28, 2018.

Extended European Search Report corresponding to Patent Application EP 18170524.5 dated Oct. 1, 2018.

Japanese Office Action corresponding to Patent Application JP 2017-536546 dated Oct. 15, 2018.

Extended European Search Report corresponding to Patent Application EP 18187640.0 dated Nov. 30, 2018.

Extended European Search Report corresponding to Patent Application EP 18187690.5 dated Nov. 30, 2018.

Chinese First Office Action corresponding to Patent Application CN 201510696298.9 dated Dec. 3, 2018.

Extended European Search Report corresponding to Patent Application EP 18158143.0 dated Dec. 5, 2018.

The Extended European Search Report corresponding to EP 08 73 2820.9, completed Jul. 2, 2013 and dated Jul. 9, 2013; (10 Pages).

(56) References Cited

OTHER PUBLICATIONS

The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 14 15 1673.2, completed Sep. 3, 2014 and dated Sep. 12, 2014; (14 pp).
Extended European Search Report corresponding to counterpart Int'l Appln. No. EP 16 15 0739.7 dated May 17, 2016.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
Chinese First Office Action corresponding to Int'l Appln. No. CN 201410076318.8 dated Jan. 23, 2017.
Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.
Extended European Search Report corresponding to EP 10 25 2112.7, completed Jul. 29, 2014 and dated Aug. 5, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
Partial European Search Report corresponding to EP 14 15 1673.2, completed Apr. 25, 2014 and dated May 8, 2014; (8 pp).
The extended European Search Report corresponding to European Application No. EP 07 25 3905.9, completed Jan. 29, 2008; dated Feb. 7, 2008; (7 Pages).
The partial European Search Report corresponding to European Application No. EP 07 25 3807.7, completed Jul. 23, 2008; dated Aug. 1, 2008; (3 pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 380.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).

(56) References Cited

OTHER PUBLICATIONS

The extended European Search Report corresponding to European Application No. EP 09 25 20515, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
Chinese Second Office Action corresponding to counterpart Int'l Appln. No. CN 201410076318.8 dated Oct. 10, 2017.

* cited by examiner

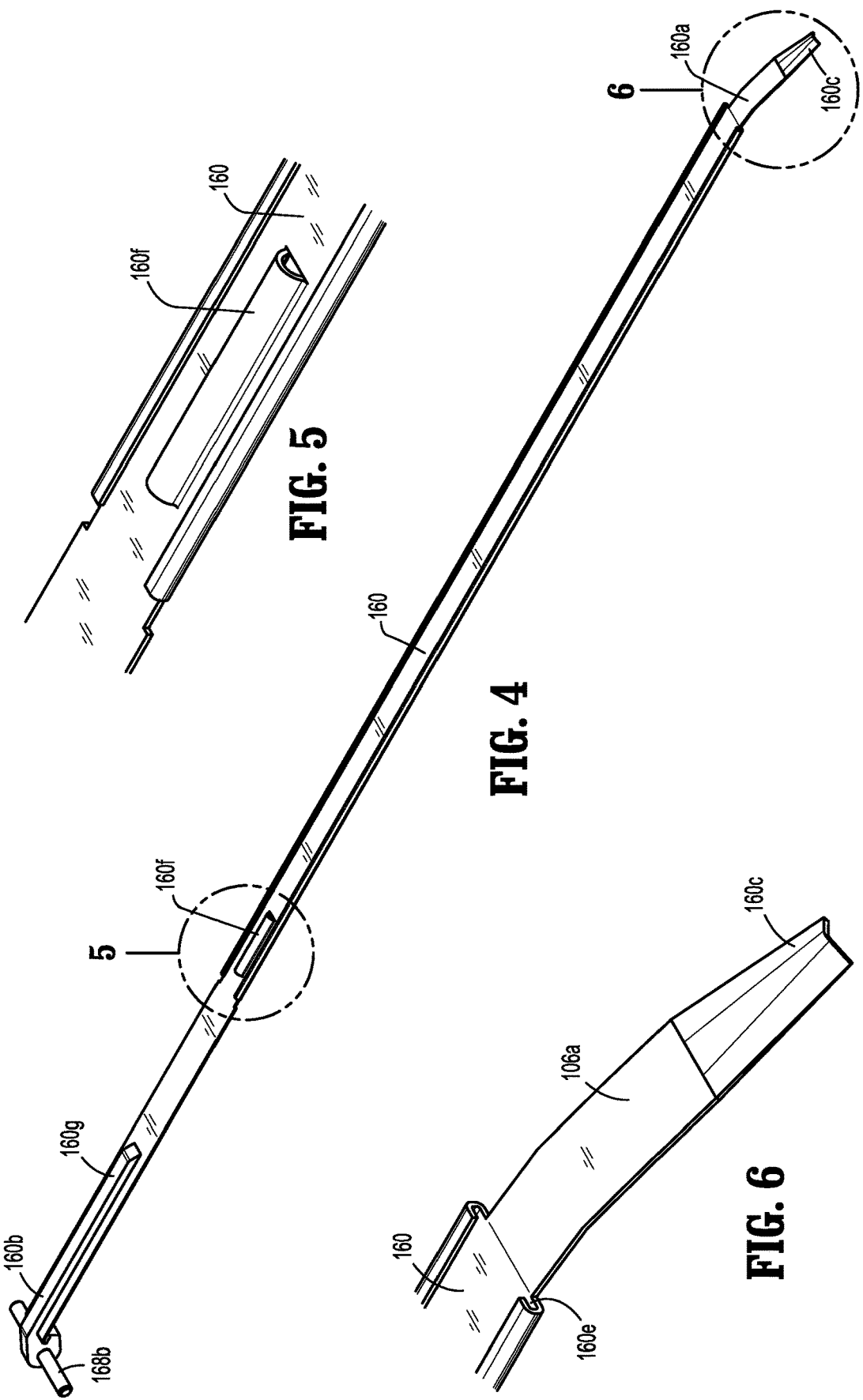

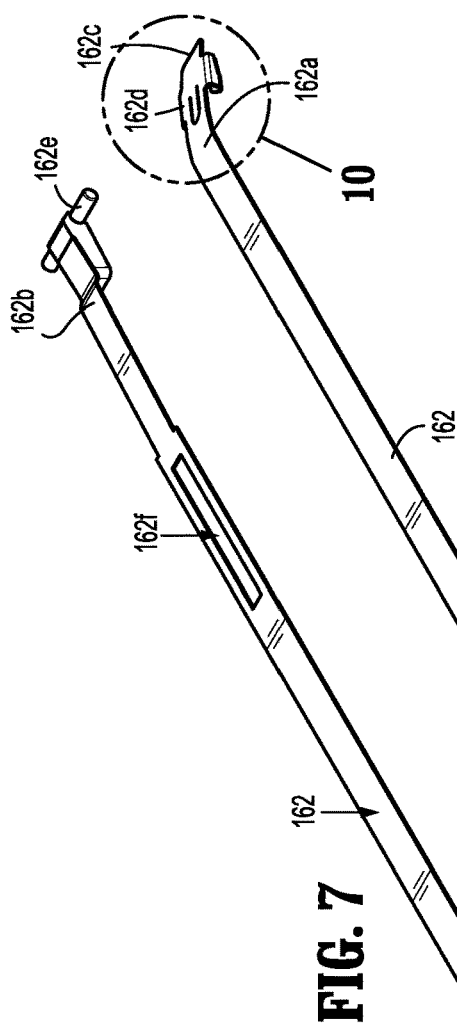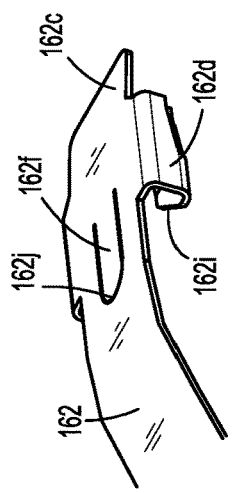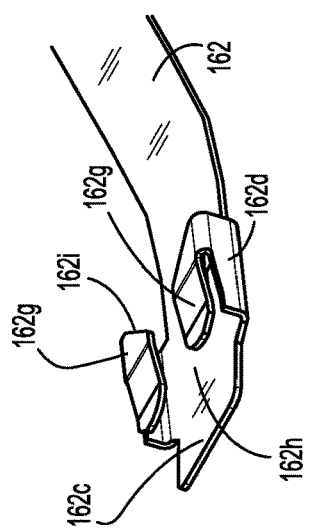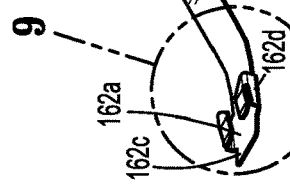
FIG. 7
FIG. 8
FIG. 9
FIG. 10

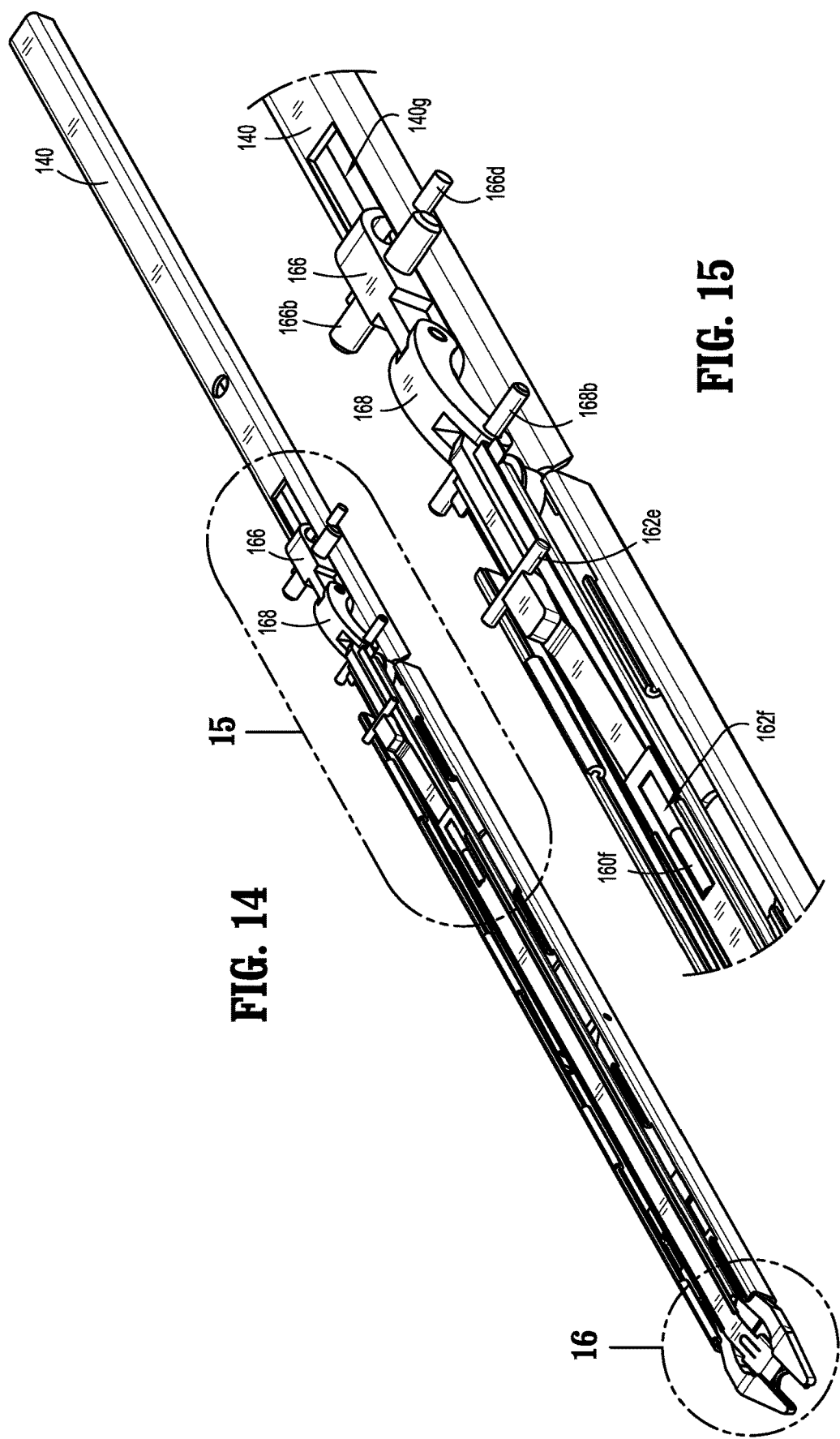

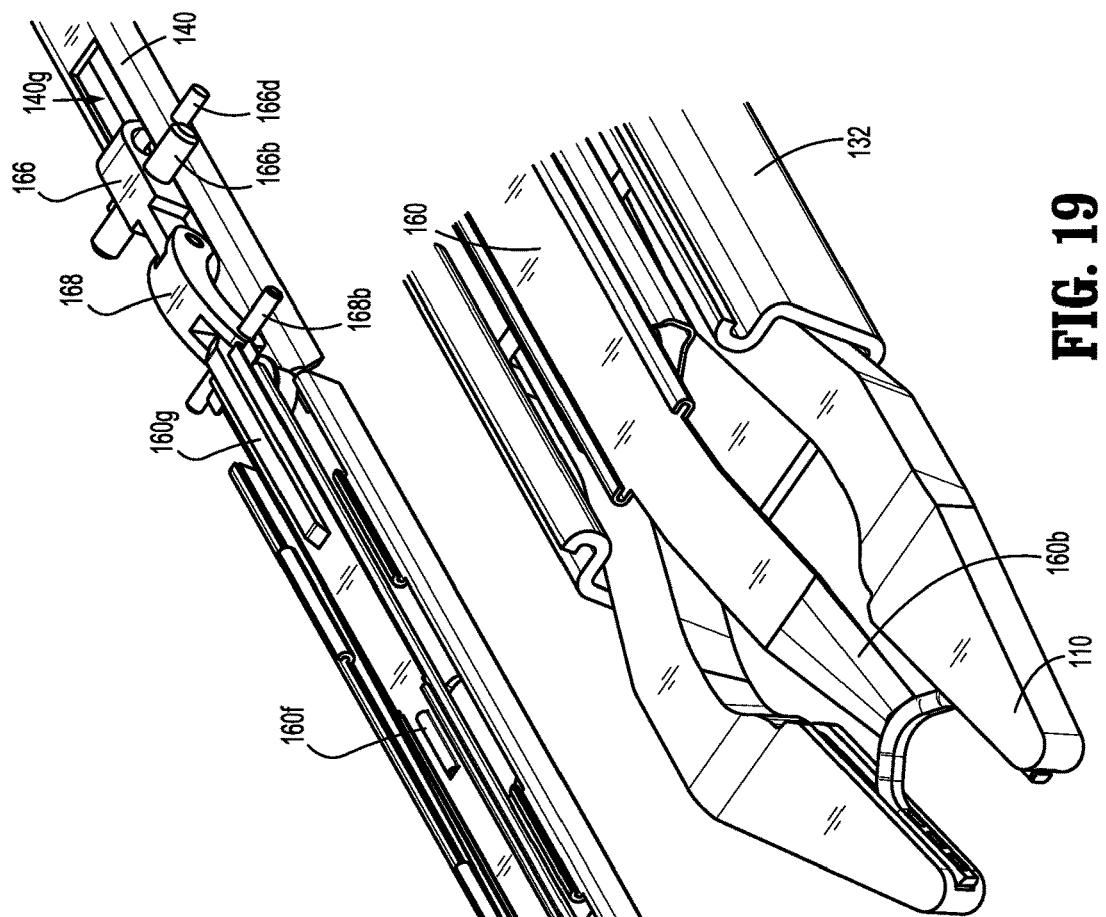
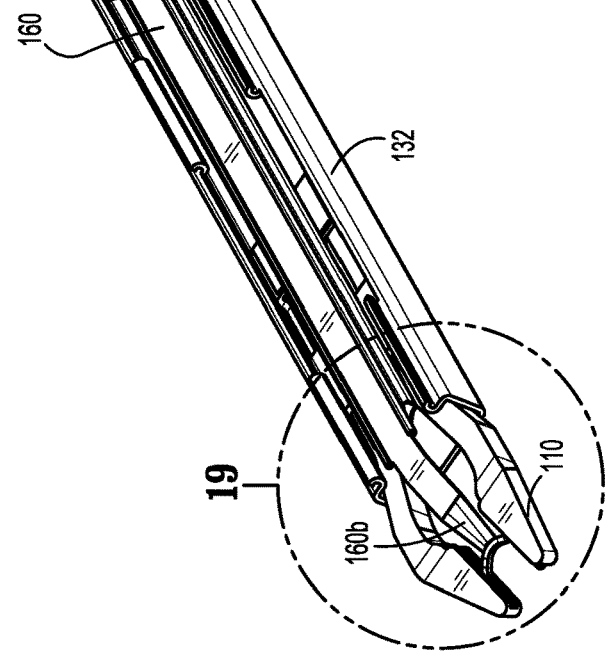
FIG. 18
FIG. 19

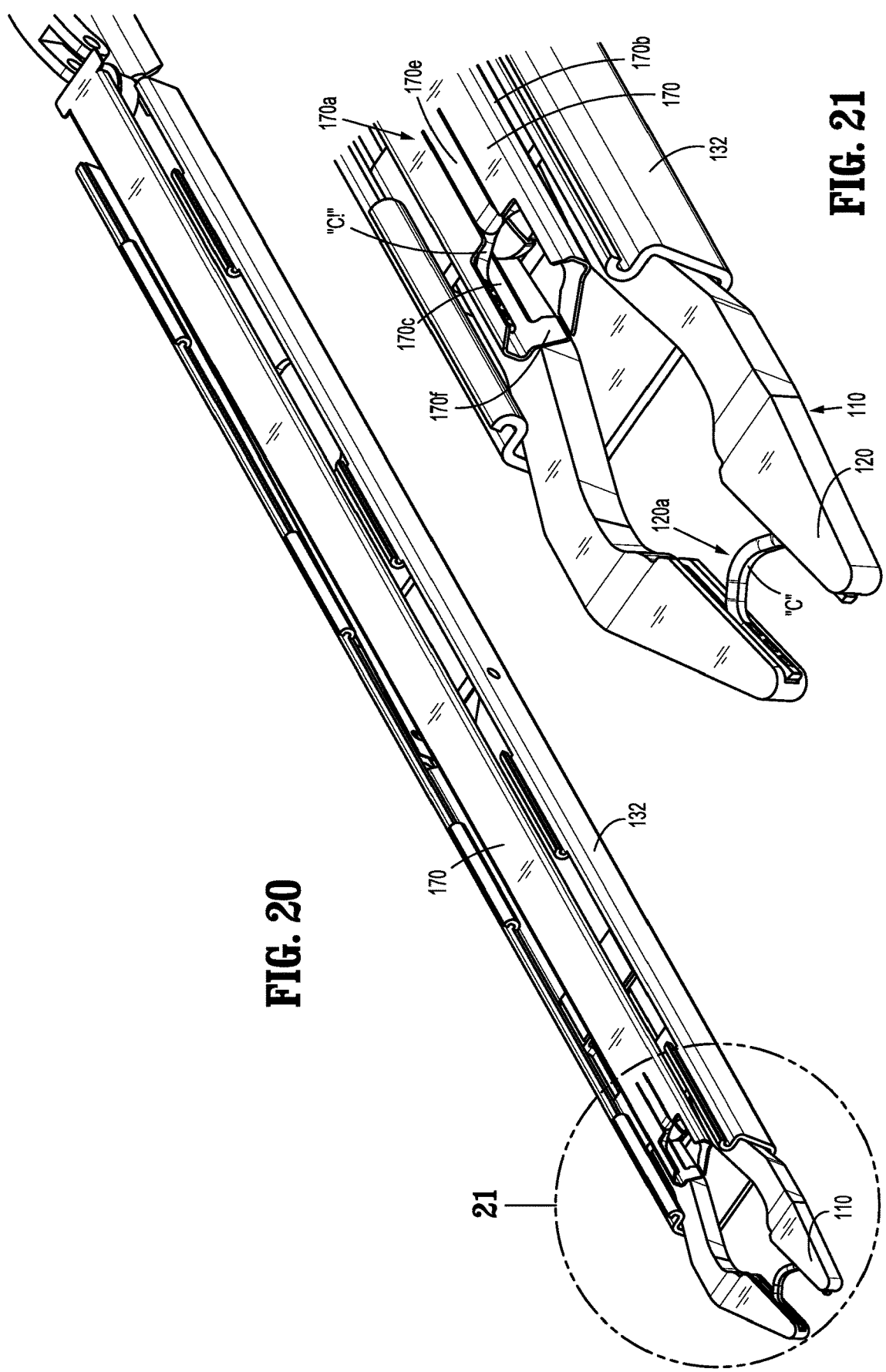

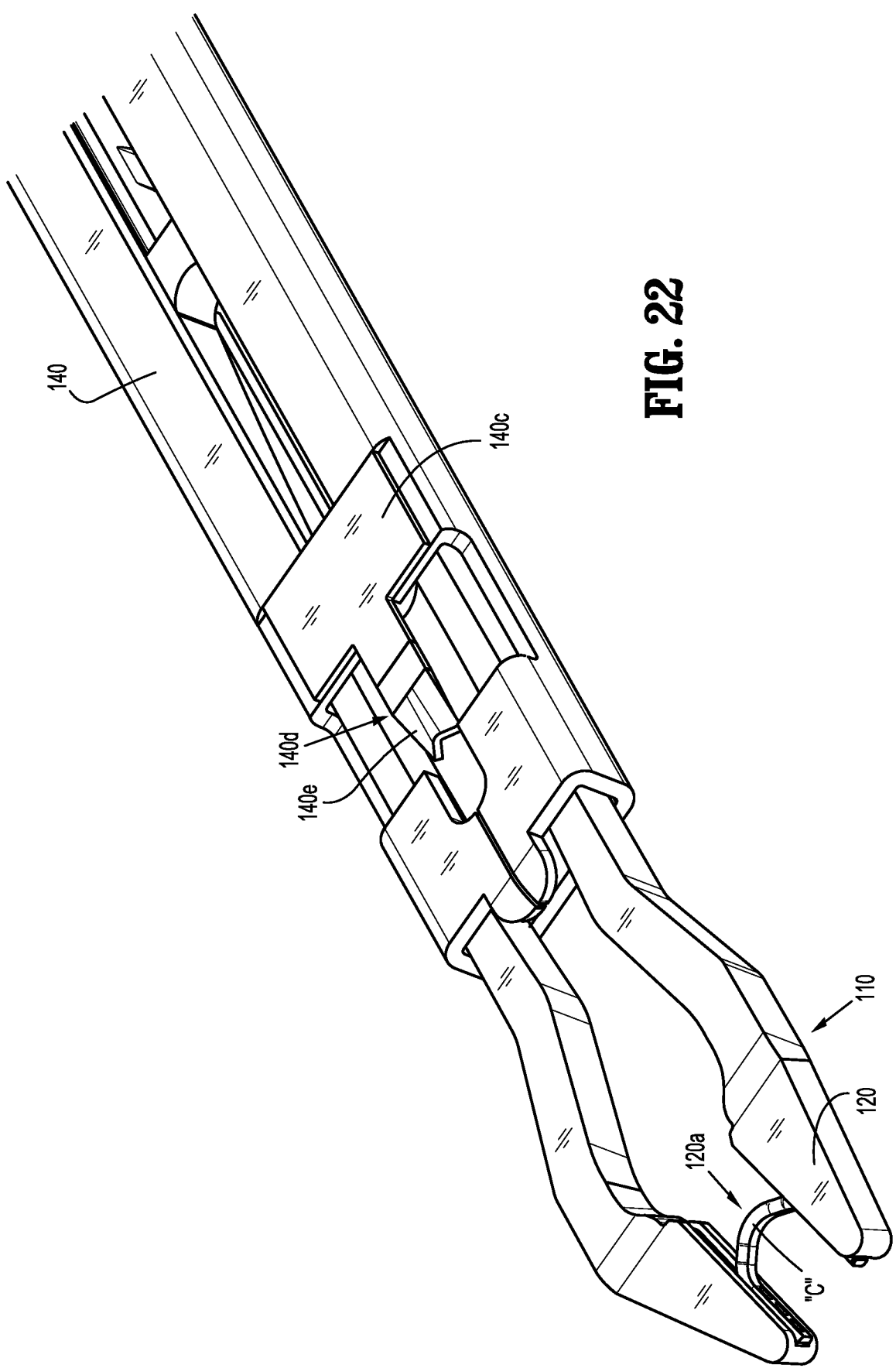

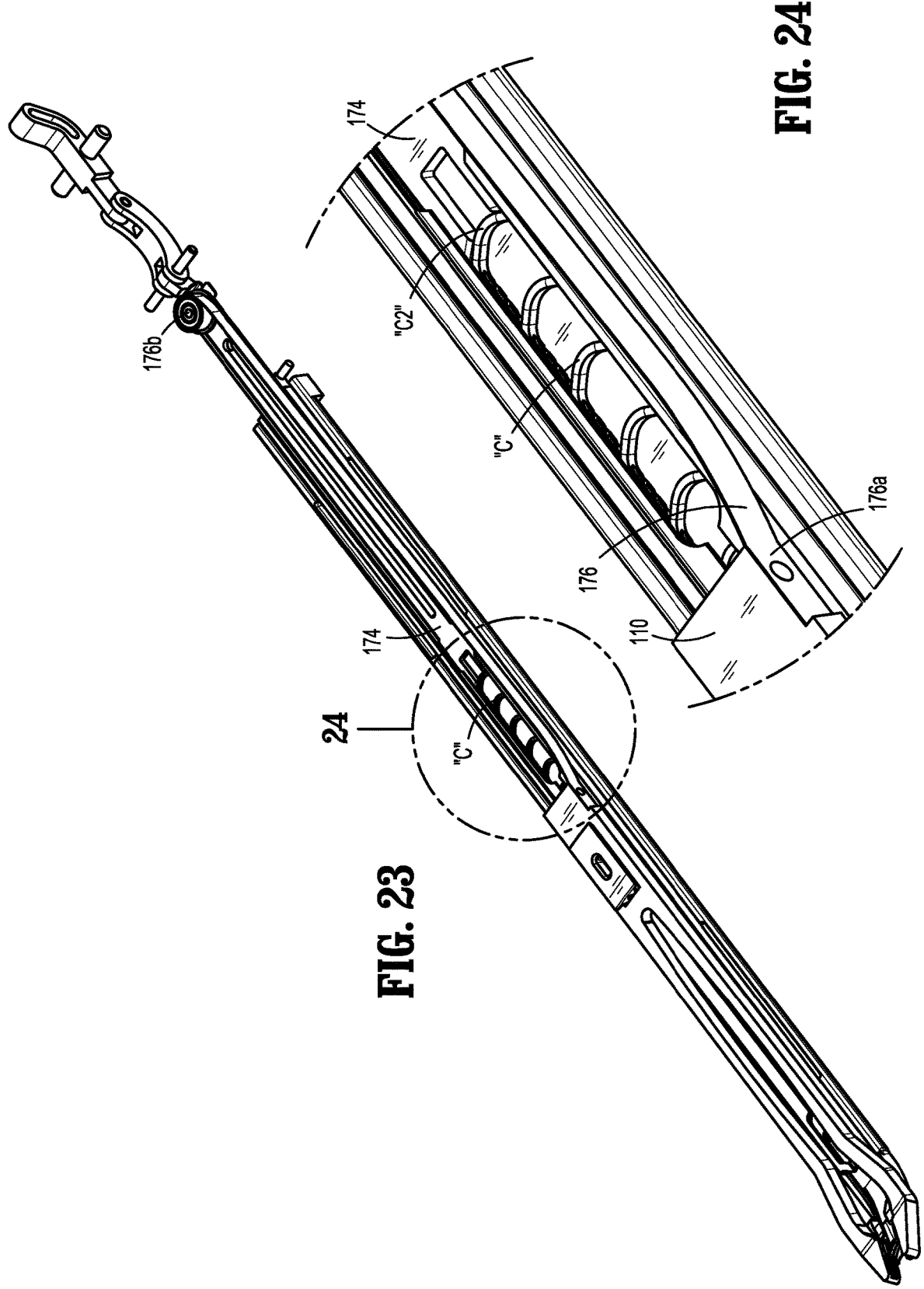

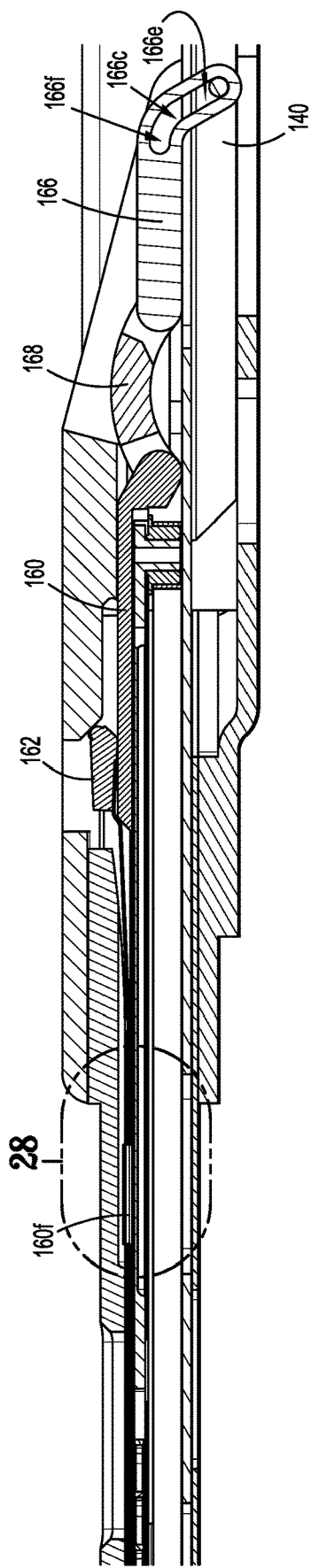
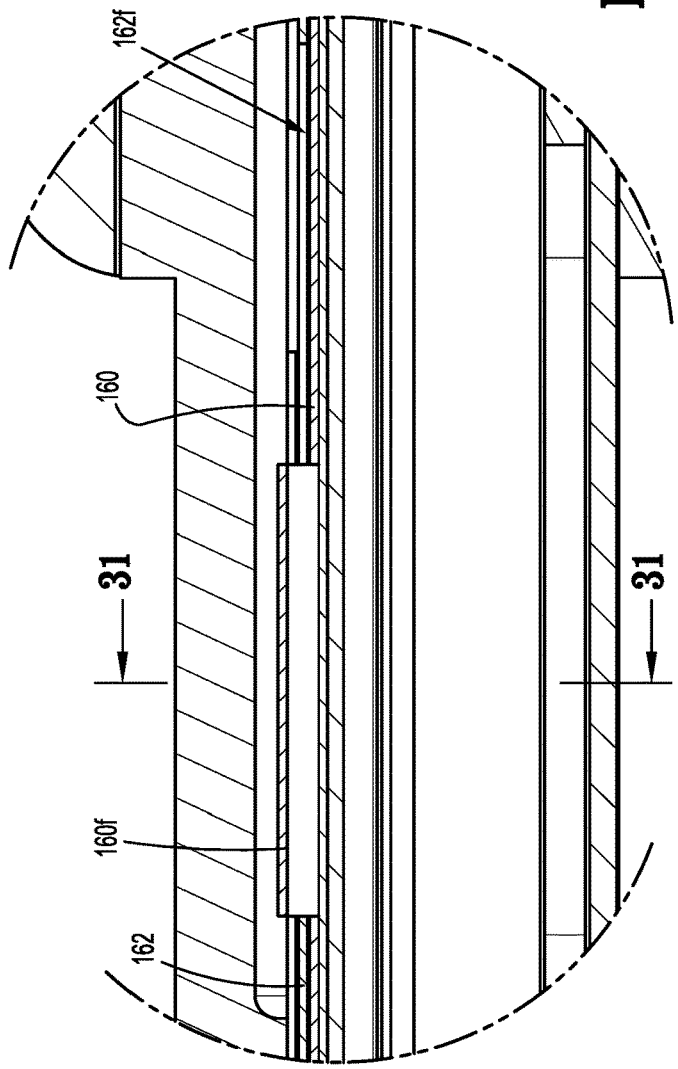
FIG. 27
FIG. 28

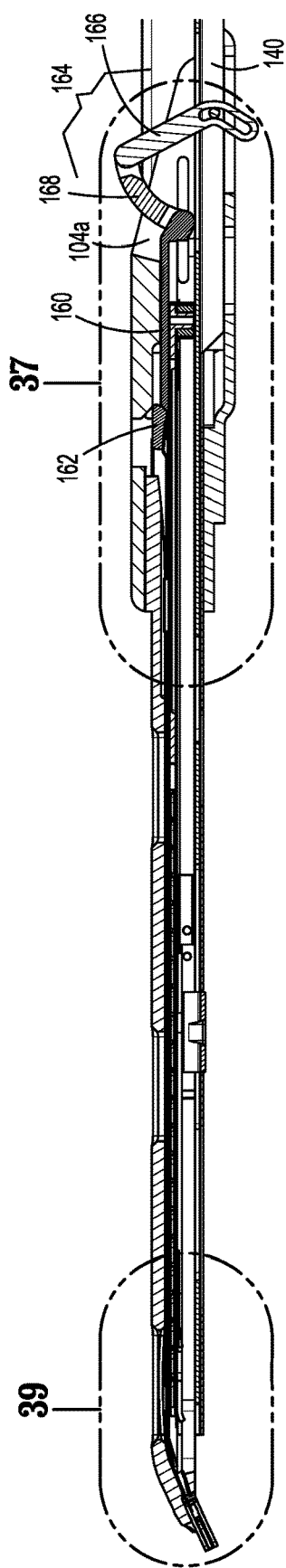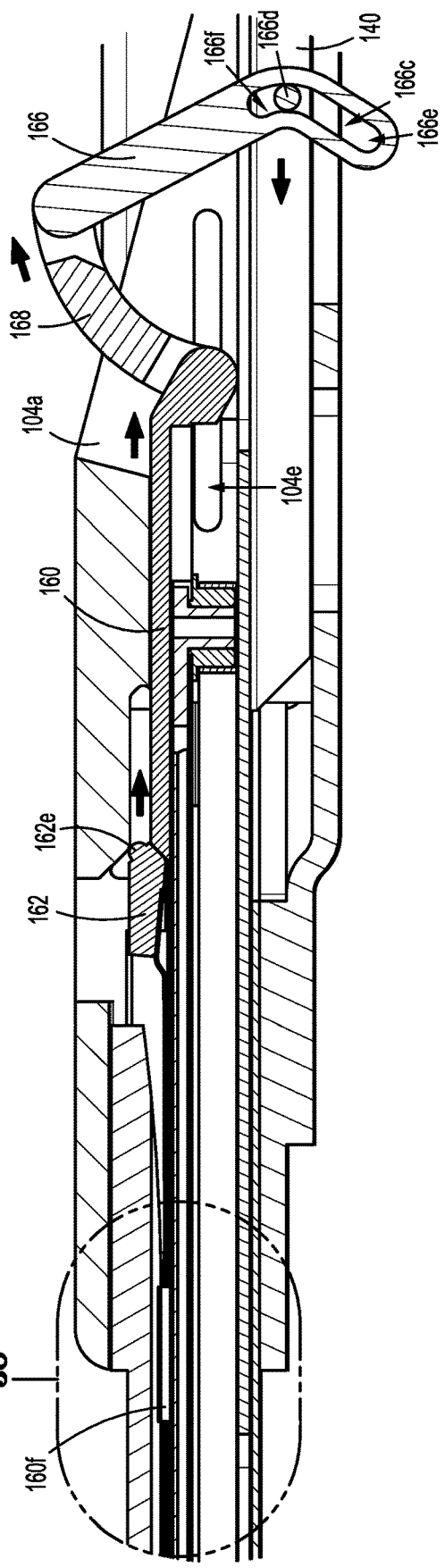
FIG. 36
FIG. 37

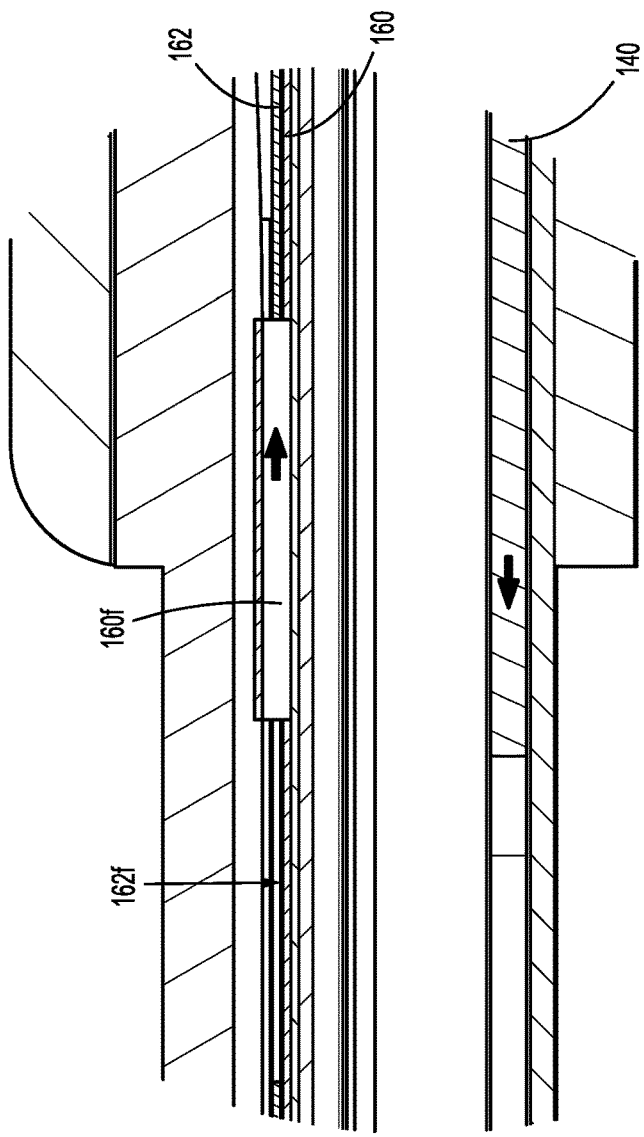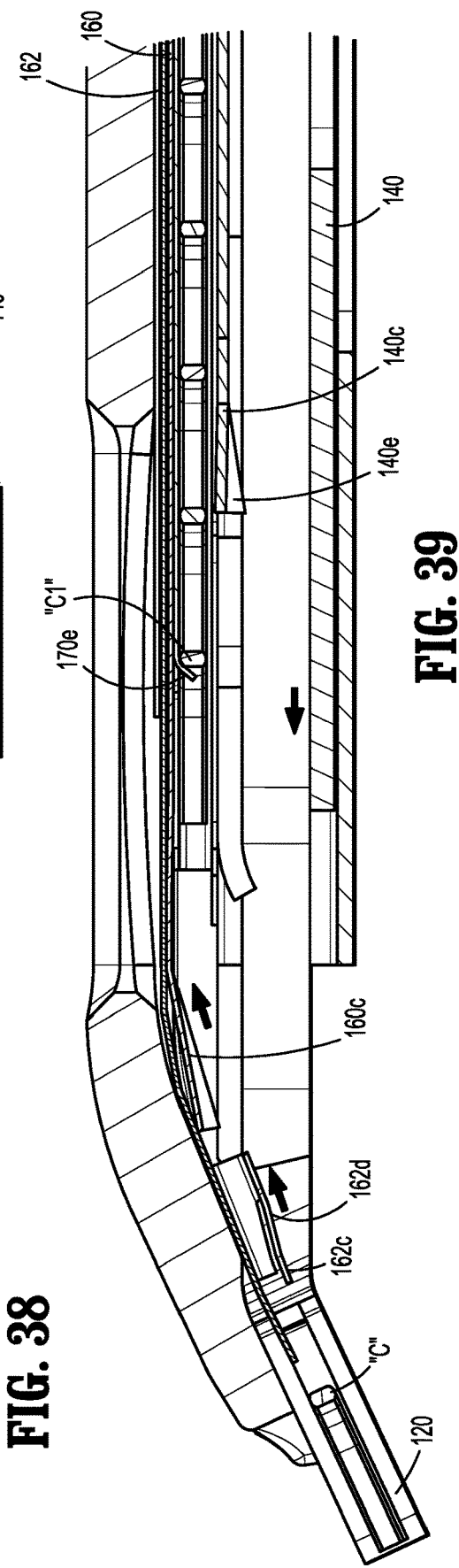
FIG. 38
FIG. 39

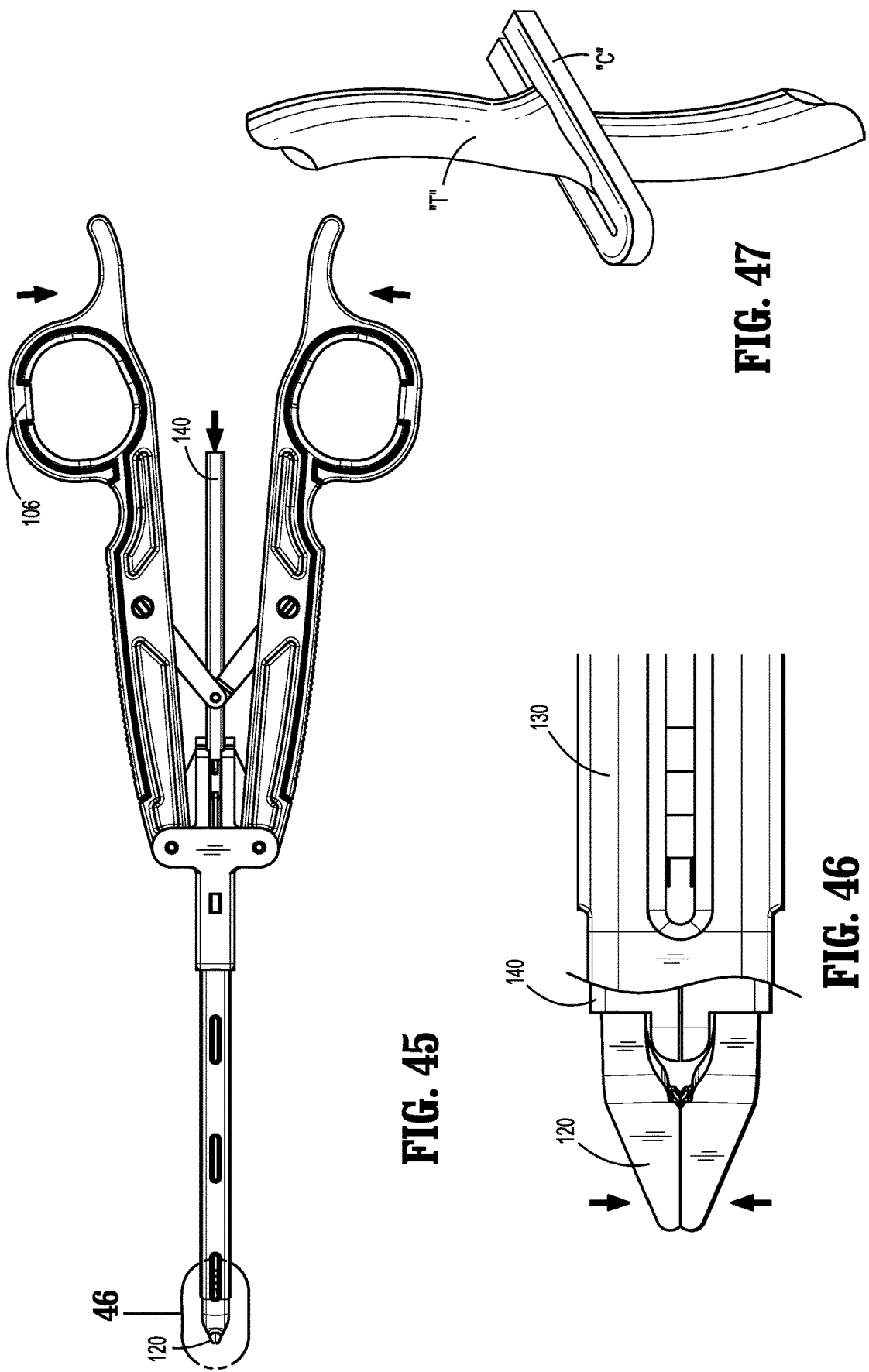

SURGICAL CLIP APPLIER

CROSS-REFERENCE TO RELATED APPLICATIONS

This application is a continuation of U.S. patent application Ser. No. 14/146,126 filed Jan. 2, 2014, which claims priority to and the benefit of U.S. Provisional Patent Application Ser. No. 61/754,143, filed on Jan. 18, 2013, and the disclosures of each of the above-identified applications are hereby incorporated by reference in their entirety.

BACKGROUND

1. Technical Field

The present application relates to surgical instruments, and more particularly, to surgical clip appliers having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

A need exists for clip applier having simplified operation using fewer components to provide a more efficient and cost effective clip applying device without diminishing functionality.

SUMMARY

The present application relates to surgical clip appliers having a plurality of clips for applying the clips to body tissues and vessels during surgical procedures and their methods of use.

According to an aspect of the present disclosure, a surgical clip applier is provided including a housing, at least one handle pivotably connected to the housing, a channel assembly extending distally from the housing, a clip carrier disposed within the channel assembly and defining a channel therein, a plurality of clips slidably disposed within the channel of the clip carrier, a jaw assembly including a pair of jaws extending from an end of the channel assembly, opposite the housing, adapted to accommodate a clip therein and being operable to effect formation of a clip in response to movement of the at least one handle, and a shuttle bar slidably supported in the channel assembly and configured to transport a clip from the clip carrier to the jaw assembly.

According to an aspect of the present disclosure, the shuttle bar includes a wedge at a distal end thereof configured for selective insertion between the jaws to maintain the jaws in an open condition.

According to an aspect of the present disclosure, the shuttle bar includes a shuttle box configured to receive a clip from the clip carrier therein for transporting to the jaw assembly.

According to an aspect of the present disclosure, the shuttle box transports a clip from the clip carrier to the jaw assembly upon distal movement of the shuttle bar.

According to an aspect of the present disclosure, the shuttle box is docked against the clip carrier when the shuttle bar is in a proximal position to receive a clip therein.

According to an aspect of the present disclosure, the shuttle box is docked against the jaw assembly when the shuttle bar is in a distal position.

According to an aspect of the present disclosure, the clip applier further includes a clip pusher bar slidably supported within at least one of the housing and the channel assembly and movable towards the jaw assembly to urge a clip from a location retained in the shuttle box to a location between the jaws.

According to an aspect of the present disclosure, the clip applier further includes a clip loader slidably supported within the channel assembly and translatable relative to the clip carrier to urge a distal most clip of the clip carrier into the shuttle box.

According to an aspect of the present disclosure, the clip carrier includes a slot adjacent the distal most clip thereof for receiving the clip loader therethrough when the clip loader translates relative to the clip carrier such that a tongue of the clip loader engages the distal most clip to urge the distal most clip into the shuttle box.

According to an aspect of the present disclosure, the clip applier further includes a drive channel slidably supported within at least one of the housing and the channel assembly having a first end operatively connected to the at least one handle and a second end configured and dimensioned to selectively engage the pair of jaws to effectuate closure of the pair of jaws. The drive channel is moved towards the jaw assembly as the at least one handle is actuated in a first direction to move the second end thereof against the jaws to close the jaws and moved away from the jaws as the at least one handle is actuated in a second direction to move the second end thereof away from the jaws to allow the jaws to open.

According to an aspect of the present disclosure, a surgical clip applier is provided including a housing, at least one handle pivotably connected to the housing, a channel assembly extending distally from the housing, a clip carrier disposed within the channel assembly and defining a channel therein, a plurality of clips slidably disposed within the channel of the clip carrier, a drive channel slidably supported within at least one of the housing and the channel assembly and operatively connected to the at least one handle, a clip pusher bar slidably supported within at least one of the housing and the channel assembly, and a linkage mechanism disposed in at least one of the housing and the channel assembly. The linkage mechanism is operatively connected to the drive channel and to the clip pusher bar and is configured to translate the pusher bar in a first direction upon translation of the drive channel in a second, opposite direction, and to maintain the clip pusher bar in position upon further translation of the drive channel.

According to an aspect of the present disclosure, the linkage mechanism includes a cam slot having a first pin slidably disposed therein and operatively connected to the drive channel. The first pin is slidable along the cam slot upon translation of the drive channel.

According to an aspect of the present disclosure, the cam slot includes a cam portion and a dwell portion. The first pin is slidable along the cam portion to cause the linkage mechanism to translate the pusher bar in the first direction upon translation of the drive channel in the second direction.

The first pin is slidable along the dwell portion to allow the linkage mechanism to maintain the pusher bar in position upon further translation of the drive channel.

According to an aspect of the present disclosure, the linkage mechanism includes a first linkage arm rotatably disposed at least partially within the housing and rotatable upon translation of the first pin along the cam portion of the cam slot to translate the pusher bar in the first direction.

According to an aspect of the present disclosure, the first pin is slidably received in a first slot of the housing and slidable along the first slot of the housing and the cam slot of the linkage mechanism during translation of the drive bar to rotate the first linkage arm relative to the housing.

According to an aspect of the present disclosure, the linkage mechanism further includes a second linkage arm rotatably secured to the first linkage arm and slidably secured to the housing by a second pin slidably disposed in a second slot of the housing. Upon rotation of the first linkage arm, the second linkage arm rotates relative to the first linkage arm and causes the second pin to slide along the second slot of the housing. The second pin is operatively connected to the pusher bar to effect translation of the pusher bar relative to the housing upon translation of the second pin along the second slot of the housing.

According to an aspect of the present disclosure, the clip applier further includes a shuttle bar slidably supported in the channel assembly and configured to transport a clip from the clip carrier to the jaw assembly. The pusher bar is configured to engage the shuttle bar after an initial translation in the first direction to translate the shuttle bar in the first direction.

According to an aspect of the present disclosure, the pusher bar includes a fin extending into a slot of the shuttle bar and configured to engage an end of the slot to translate the shuttle bar in at least the first direction.

According to an aspect of the present disclosure, the pusher bar urges a proximal portion of the shuttle bar against a cutout of the housing prior to the initial translation of the pusher bar in the first direction and subsequently releases the shuttle bar from the cutout after the initial translation of the pusher bar in the first direction to allow the shuttle bar to translate in the first direction.

According to an aspect of the present disclosure, the clip applier further includes a jaw assembly including a pair of jaws extending from an end of the channel assembly, opposite the housing. The jaw assembly is adapted to accommodate a clip therein and is operable to effect formation of a clip in response to movement of the at least one handle.

Although the above aspects and embodiments are described separately for convenience and clarity, it is contemplated that the above aspects and embodiments may be combined without departing from the scope of the present disclosure.

BRIEF DESCRIPTION OF THE DRAWINGS

The present clip applier will be more fully appreciated as the same becomes better understood from the following detailed description when considered in connection with the following drawings, in which:

FIG. 4 is a perspective view of a pusher bar of the clip applier of FIG. 1;

FIG. 5 is an enlarged view of the indicated area of detail of FIG. 4

FIG. 6 is an enlarged view of the indicated area of detail of FIG. 4;

FIG. 7 is a top, perspective view of the a shuttle bar of the clip applier of FIG. 1;

FIG. 8 is a bottom, perspective view of the shuttle bar of FIG. 7;

FIG. 9 is an enlarged view of the indicated area of detail of FIG. 7;

FIG. 10 is an enlarged view of the indicated area of detail of FIG. 8;

FIG. 14 is a perspective view of a shaft assembly and housing of the clip applier of FIG. 1;

FIG. 15 is an enlarged view of the indicated area of detail of FIG. 14;

FIG. 18 is a perspective view of the shaft assembly and housing of FIG. 14 with the cover and a shuttle bar removed therefrom;

FIG. 19 is an enlarged view of the indicated area of detail of FIG. 18;

FIG. 20 is a perspective view of the shaft assembly and housing of FIG. 14 with the cover, shuttle bar, and pusher bar removed therefrom;

FIG. 21 is an enlarged view of the indicated area of detail of FIG. 19;

FIG. 22 is an enlarged view of the distal end of the shaft assembly of FIG. 20 with the clip carrier removed therefrom;

FIG. 23 is a bottom, perspective view of the shaft assembly and housing of FIG. 14 with the lower channel removed therefrom;

FIG. 24 is an enlarged view of the indicated area of detail of FIG. 23;

FIG. 27 is an enlarged view of the indicated area of detail of FIG. 26;

FIG. 28 is an enlarged view of the indicated area of detail of FIG. 27;

FIG. 36 is a side, cross-sectional view of the surgical clip applier of FIG. 35;

FIG. 37 is an enlarged view of the indicated area of detail of FIG. 36;

FIG. 38 is an enlarged view of the indicated area of detail of FIG. 37;

FIG. 39 is an enlarged view of the indicated area of detail of FIG. 36;

FIG. 45 is a top, plan view of the surgical clip applier of FIG. 35, illustrating the handles in a fully squeezed condition;

FIG. 46 is an enlarged view of the indicated area of detail of FIG. 45;

FIG. 47 is a perspective view illustrating a clip formed with tissue or a vessel grasped therein;

DETAILED DESCRIPTION OF EMBODIMENTS

Figure 1:
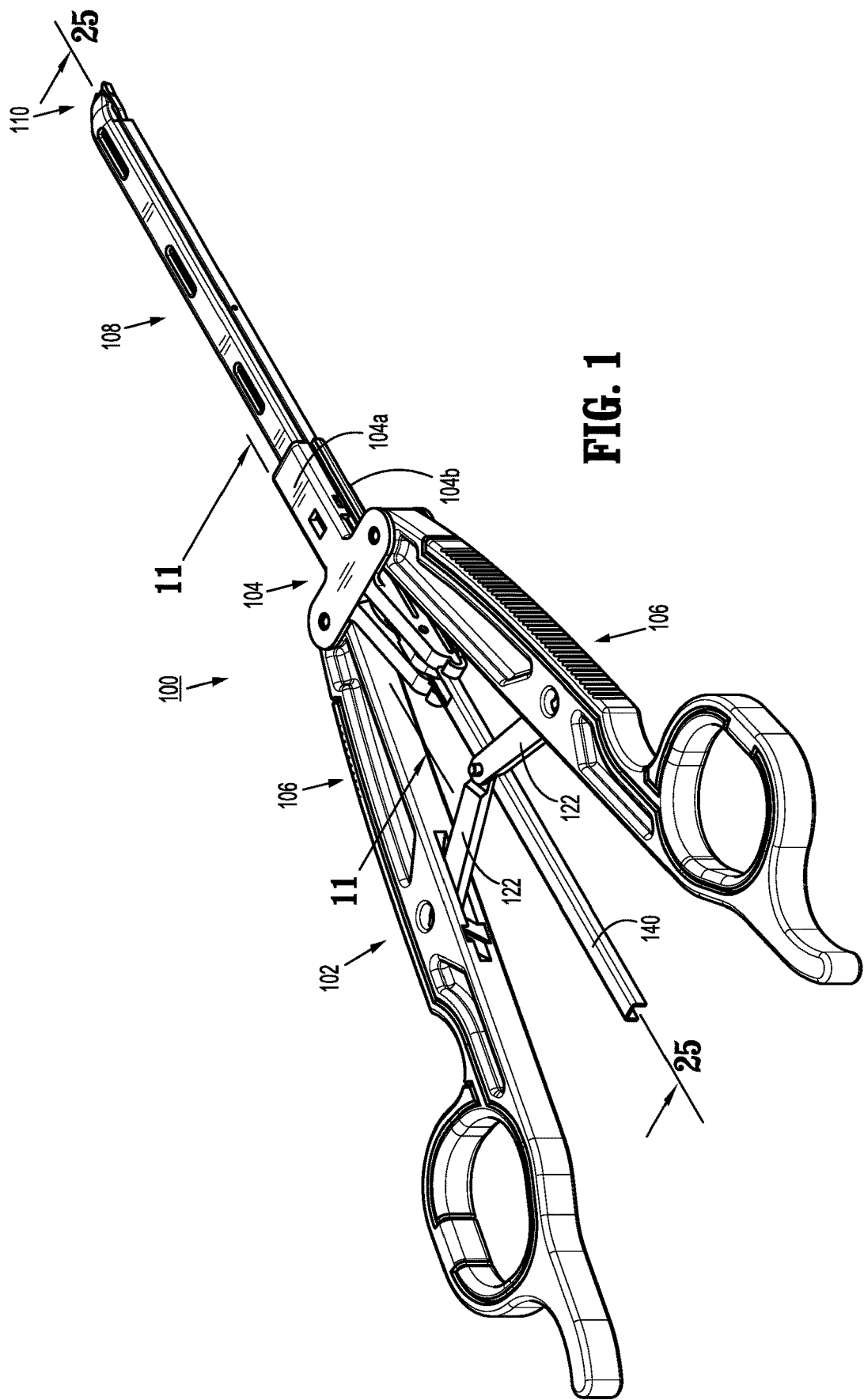
FIG. 1 is a top, perspective view of a surgical clip applier according to an embodiment of the present disclosure, with housing half-sections removed therefrom.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
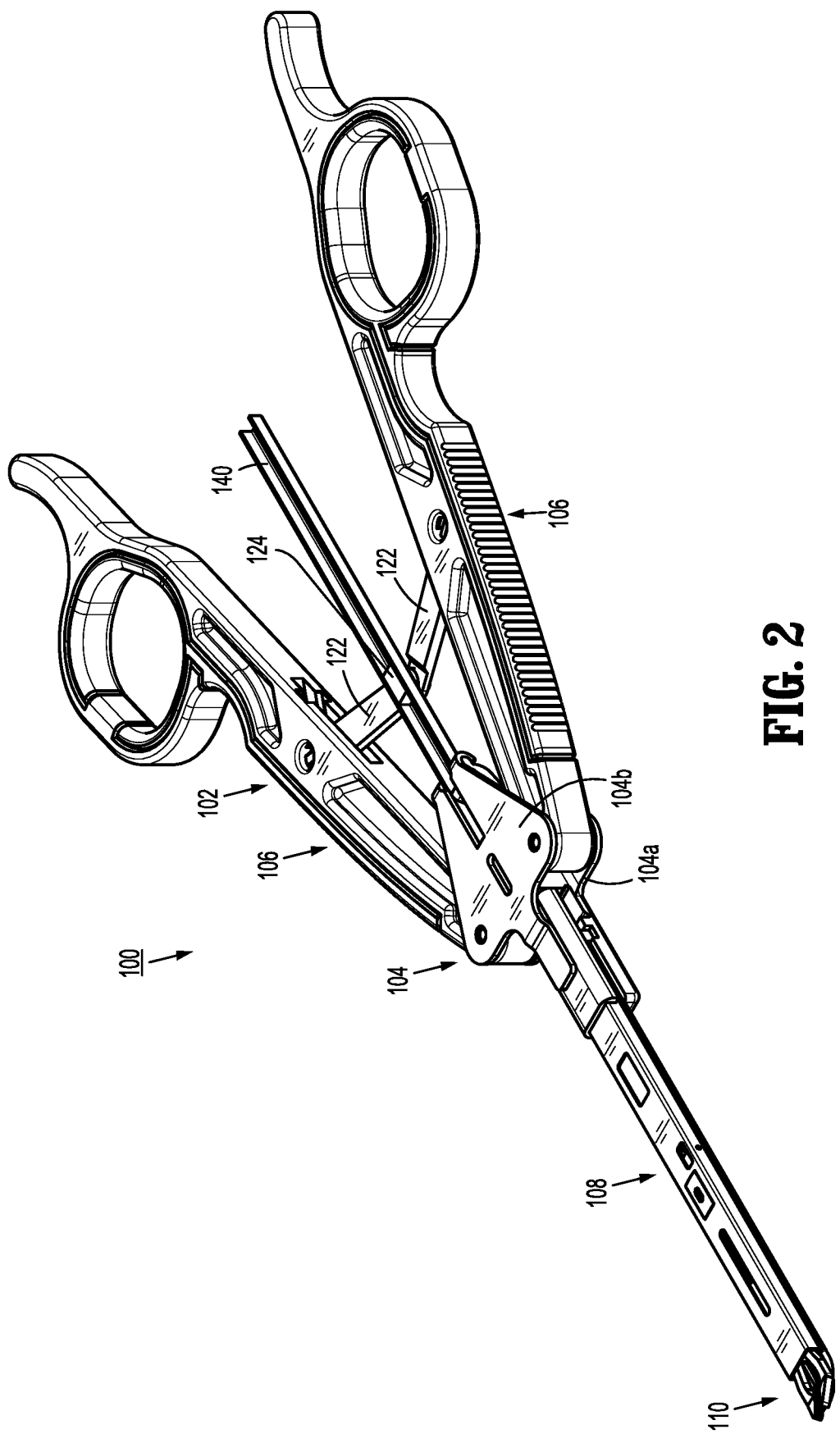
FIG. 2 is a bottom, perspective view of the surgical clip applier of FIG. 1.
Figure 3:
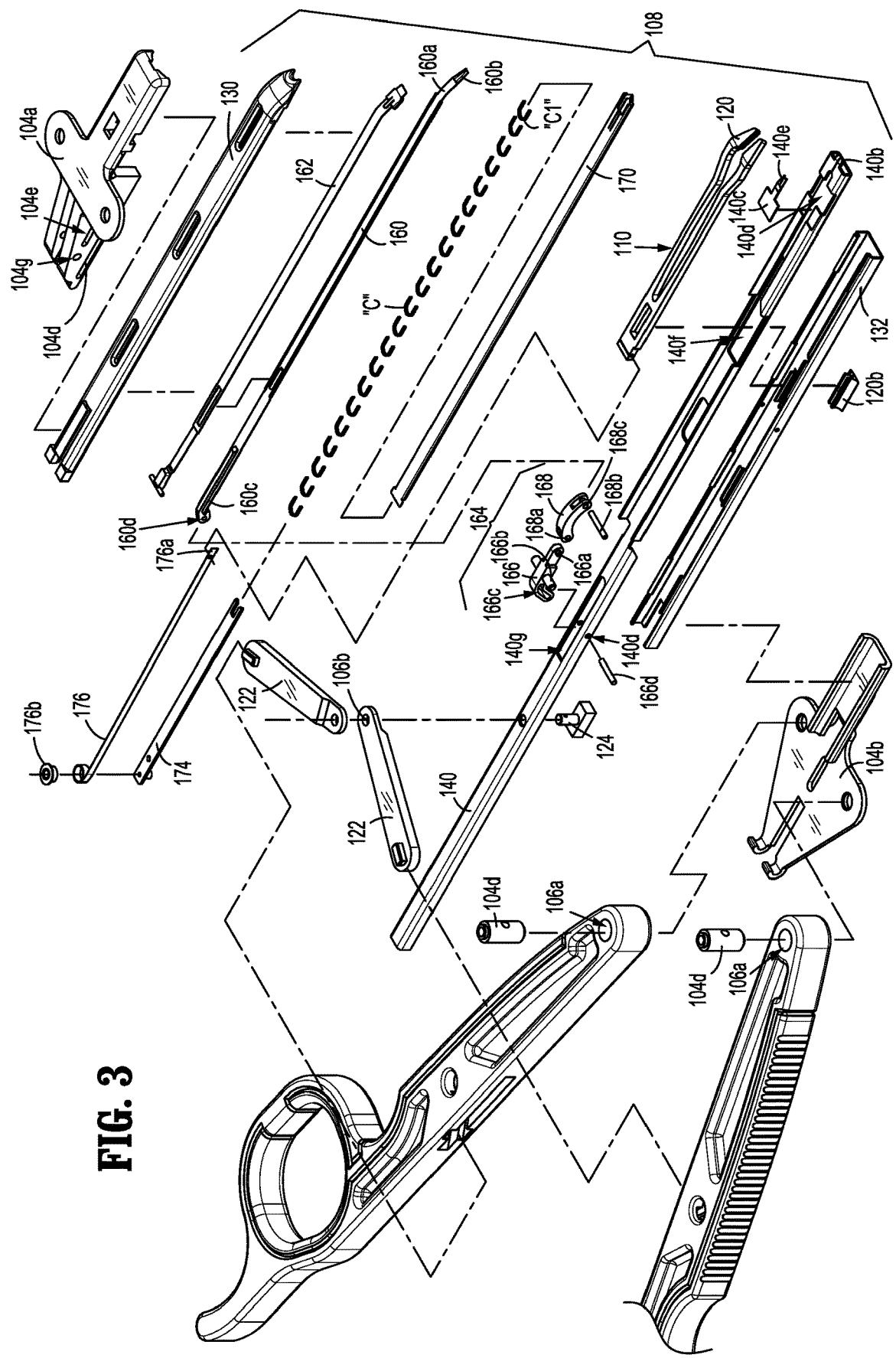
FIG. 3 is an exploded perspective view of the surgical clip applier of FIGS. 1-2.

Referring now to FIGS. 1-3, a surgical clip applier in accordance with an embodiment of the present disclosure is generally designated as 100. Surgical clip applier 100 generally includes a handle assembly 102 including an inner housing 104 having an upper housing half 104a and lower housing half 104b. Another housing of clip applier 100 has not been shown. Handle assembly 102 further includes a pair of handles 106 pivotably secured to inner housing 104 and extending outwardly therefrom. A channel assembly 108 is fixedly secured to inner housing 104 and extends distally therefrom, terminating in a jaw assembly 110 supported in a distal end of channel assembly 108. As seen in FIGS. 1-3, housing halves 104a and 104b of clip applier 100 fit together by, e.g., snap fit engagement with one another. Alternatively, housing halves 104a and 104b may be joined through one or more screws, fasteners and the like, or through the use of glues, or other adhesives.

As seen in FIG. 3, handles 106 are secured to inner housing 104 by handle pivot pins 104d extending between lower housing half 104b and upper housing 104a through respective apertures 106a formed in handles 106. Handle assembly 102 includes a link member 122 pivotally connected to each handle 106 at a pivot point 106b formed in a respective handle 106. A distal end of each link member 122 is pivotally connected to a pivot point formed in a drive channel 140 via a drive pin 124. Drive pin 124 is received through an opening 140a in drive channel 140. In use, as will be described in greater detail below, as handles 106 are squeezed, link members 122 push drive channel 140 distally via drive pin 124.

Channel assembly 108 includes a channel or cartridge cover 130 and an outer or lower channel 132 each having a proximal end retained in housing assembly 102, between upper and lower housing halves 104a, 104b.

Figure 40:
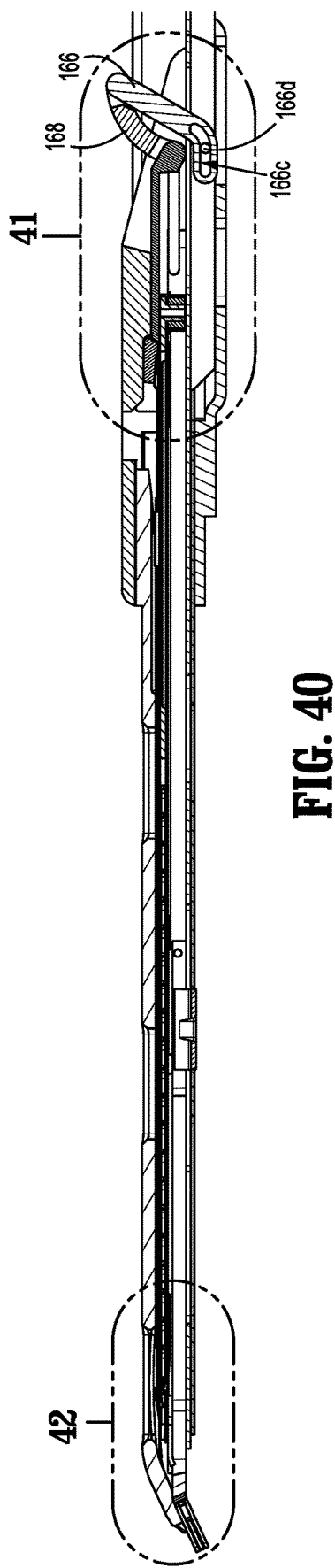
FIG. 40 is a side, cross-sectional view of the surgical clip applier of FIG. 35 during a continued squeezing on the handles.

As seen in FIGS. 3-6, clip applier 100 includes a clip pusher bar 160 slidably disposed beneath cartridge cover 130. Pusher bar 160 includes a distal end 160a defining a pusher 160c configured and adapted to selectively engage/move a distal-most clip "C1" (FIG. 3) of a stack of clips "c" stored in surgical clip applier 100. Pusher bar 160 further includes a proximal end 160b defining an opening 160d for the reception of a pin 168b of a linkage mechanism 164 therethrough. Pusher bar 160 further includes a channel 160e extending along at least a portion of its length thereof for the sliding reception of a shuttle bar 162, as will be described in greater detail below. Pusher bar 160 further includes an elongate raised portion or fin 160f for engagement with a slot 162f of shuttle bar 162 for transmitting translation of pusher bar 160 to shuttle bar 162, as will be described in greater detail below. Pusher bar 160 also includes a raised portion or rib 160g extending from proximal end 160b and configured to inhibit proximal translation of shuttle bar 162 when pusher bar 162 is in a distal most position (FIG. 40).

As seen in FIGS. 3 and 7-10, clip applier 100 includes a shuttle bar 162 slidably disposed within channel 160e of pusher bar 160. Shuttle bar 162 includes a distal end 162a defining a wedge 162c and a shuttle box 162d. Wedge 162c is configured for selective insertion between jaw members 110 to maintain jaw members 110 in a spaced apart condition when shuttle bar 162 is in a distal position. Shuttle box 162d is configured to receive the distal most clip "C1" of clip carrier 170 and transport the distal most clip "C1" to jaw members 110 upon distal translation of shuttle bar 162, as will be described in greater detail below.

Shuttle bar 162 further includes a proximal end 162b including a transverse pin 162e extending therefrom for engagement with upper housing 104a. Pin 162e is slidably engaged with a longitudinal groove 104f (FIG. 11) of upper housing 104a and is engagable with a slot or cutout 104h (FIG. 11) of upper housing 104a when shuttle bar 162 is in a distal most position. For example, in use, as pusher bar 160 translates distally, raised portion 160g thereof engages against and drives proximal end 162b of shuttle bar 162 upward with pin 162e slotting into the cutout 104h of upper housing 104a. Shuttle bar 162 further includes a slot 162f extending along at least a portion of its length for the reception of fin 160f of pusher bar 160. Slot 162f and fin 160f are configured to transmit translation of pusher bar 160 to shuttle bar 162, as will be described in greater detail below.

Shuttle box 162d includes a pair of arms 162g forming a channel or slot 162h for the reception of a clip "C", e.g., distal most clip "C1", therein. Shuttle box 162d is configured to dock against a distal end of clip carrier 170 with arms 162g of shuttle box 162d including angled surfaces 162i for engagement with corresponding angled arms 170f (FIG. 44) of clip carrier 170. Shuttle box 162d is configured to transport to and load the distal most clip "C1" into jaw assembly 110. Shuttle box 162d further includes a cutout 162j (FIG. 43) having a flexible tab 162k (FIG. 43) that is configured to provide pusher 160c with clearance during translation of pusher bar 160 relative to shuttle bar 162.

Figure 11:
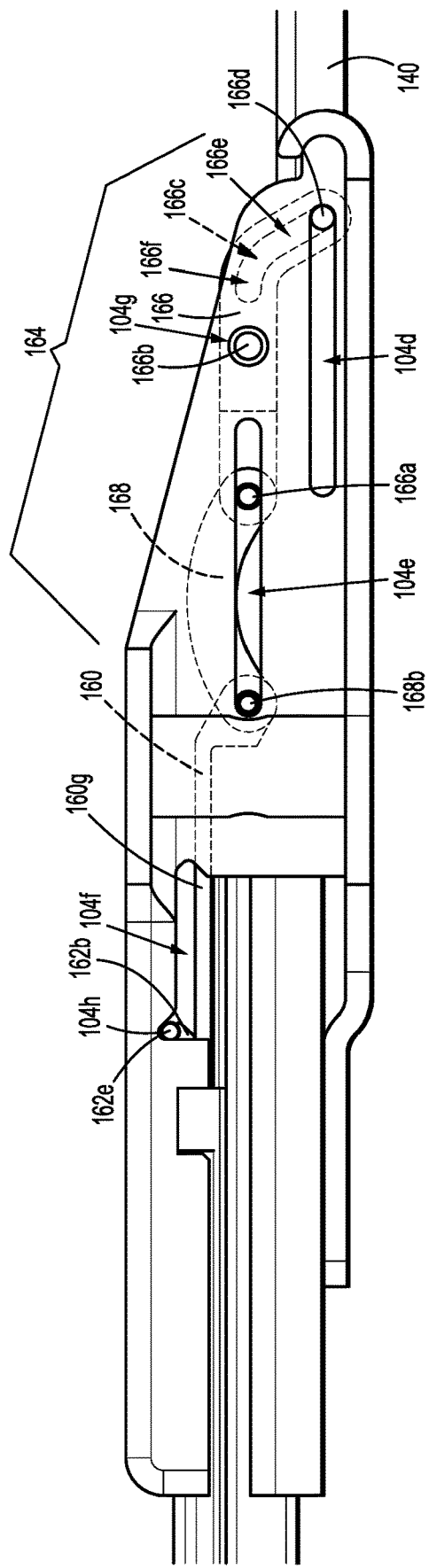
FIG. 11 is a side view of a housing of the clip applier as viewed along 11-11 of FIG. 1.
Figure 12:
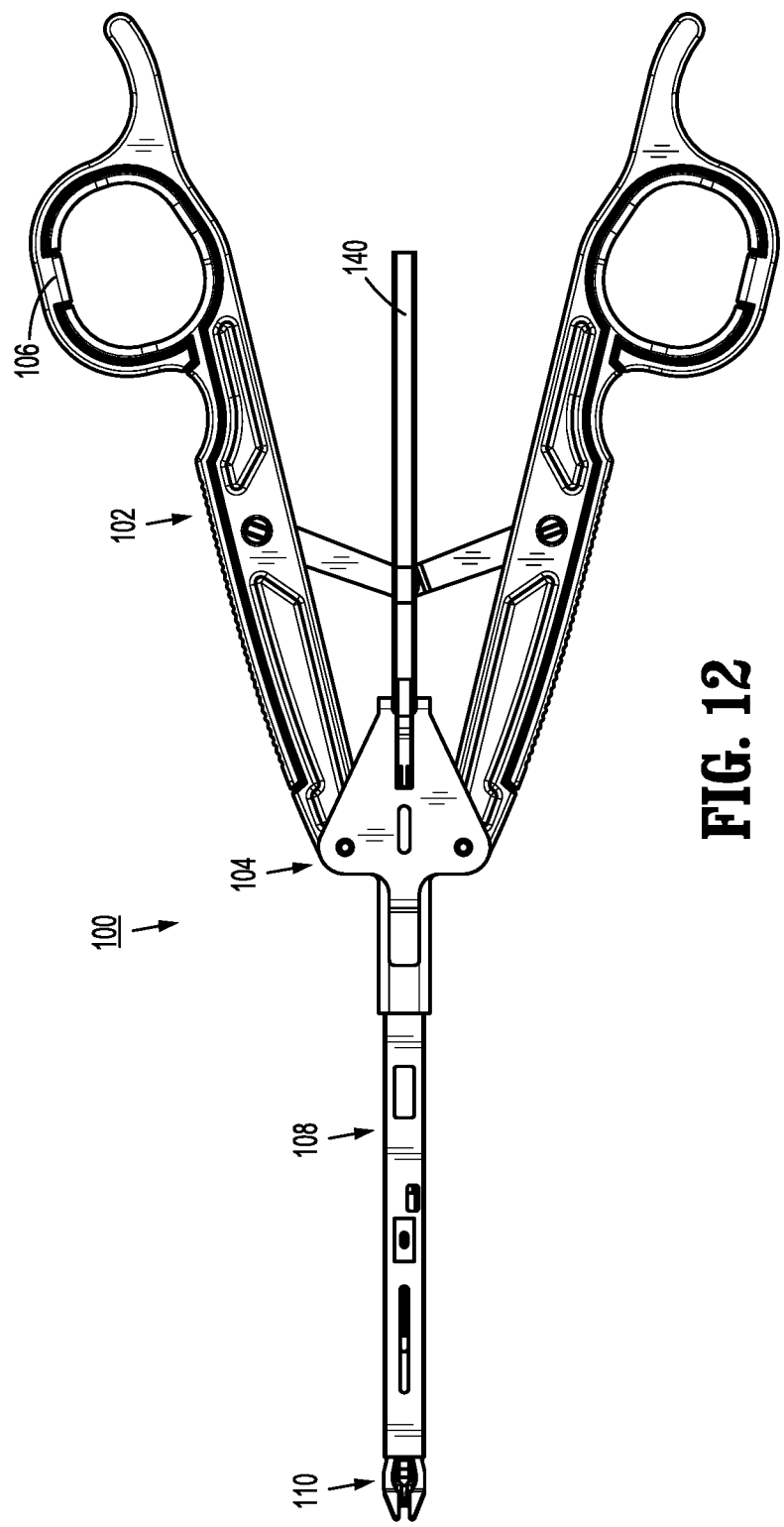
FIG. 12 is a top, plan view of the clip applier of FIG. 1.
Figure 13:
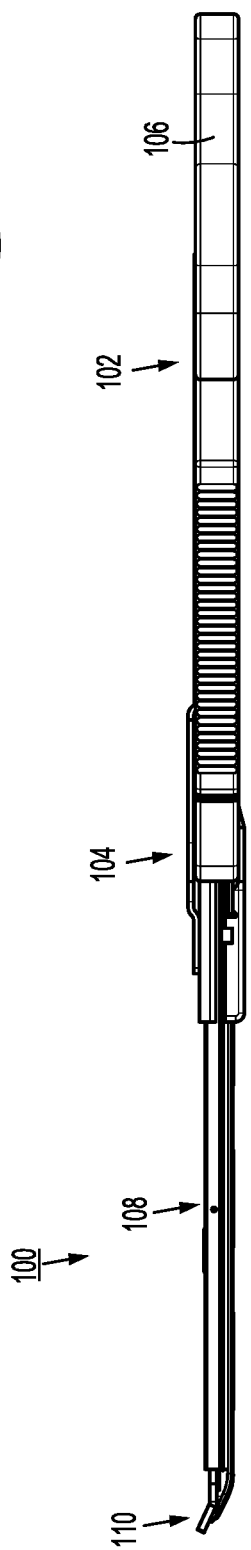
FIG. 13 is a side, elevational view of the clip applier of FIG. 1.
Figure 16:
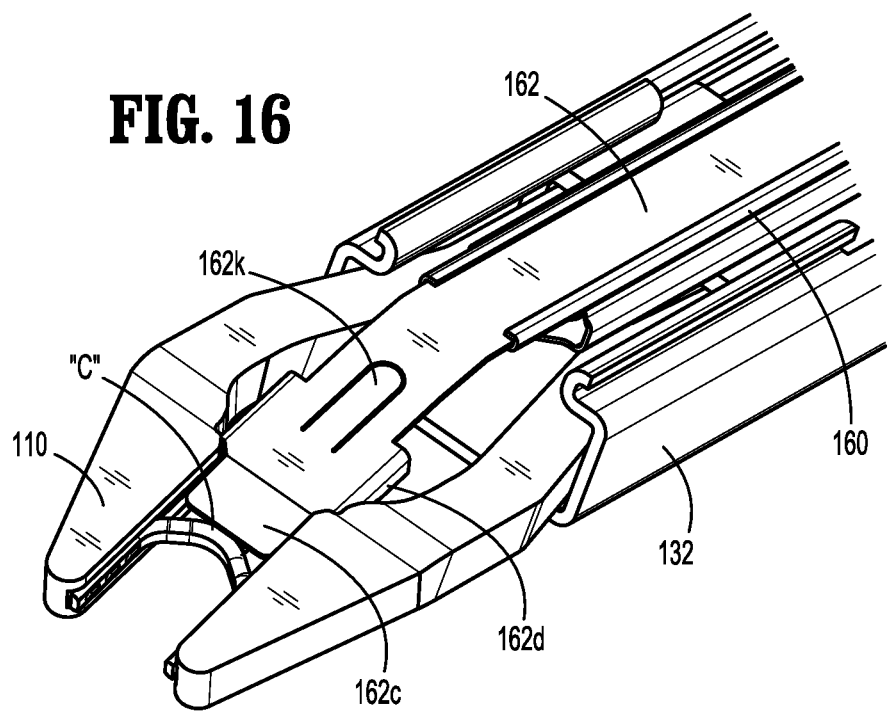
FIG. 16 is an enlarged view of the indicated area of detail of FIG. 14.
Figure 17:
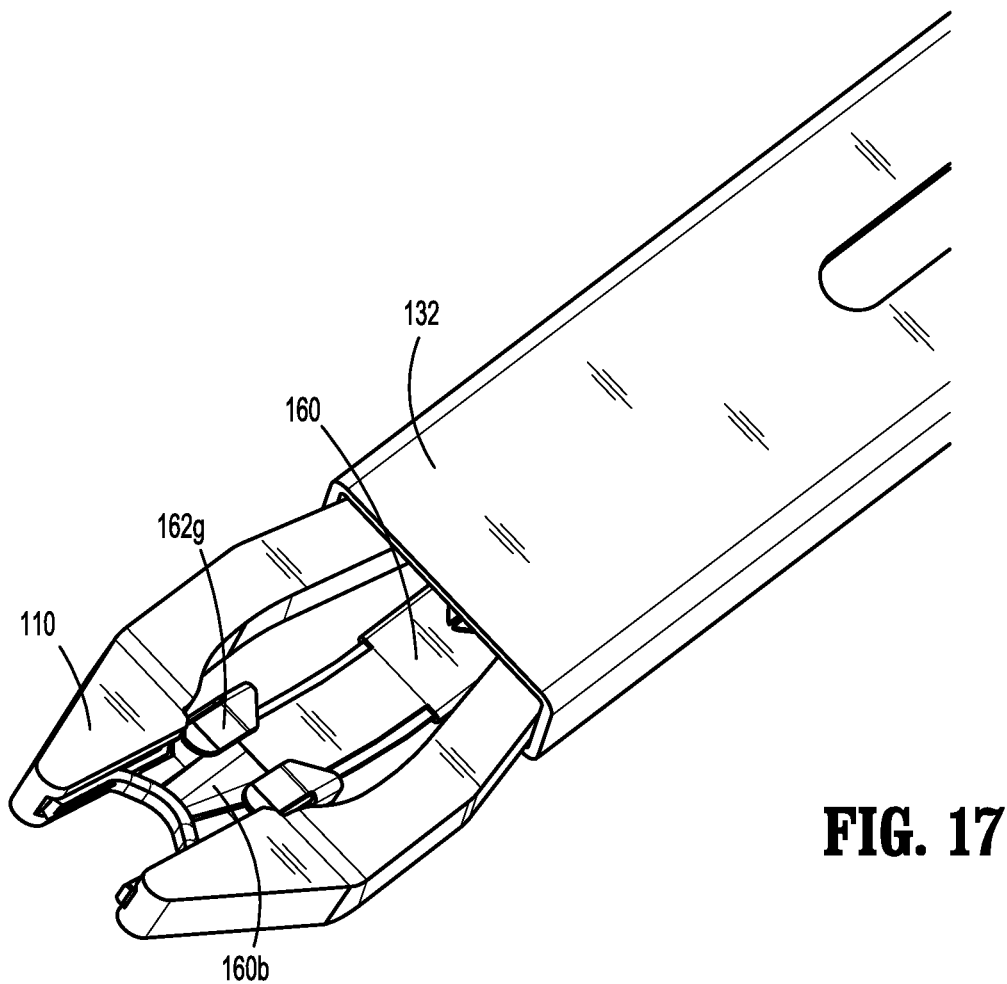
FIG. 17 is bottom, a perspective view of the enlarged view of FIG. 16.

As seen in FIGS. 3 and 11, clip applier 100 includes a linkage mechanism 164 having a first linkage arm 166 slidably and pivotally secured to drive channel 140 and a second linkage arm 168 pivotally secured to pusher bar 160. Protrusions 166a of first linkage arm 166 are pivotally secured in openings 168a of second linkage arm 168 to allow first linkage arm 166 to pivot relative to second linkage arm 168.

First linkage arm 166 is pivotally or rotatably secured to upper inner housing 104a by a pair of protrusions or nubs 166b extending through holes 104g of upper housing 104a. First linkage arm 166 includes a cam slot 166c for the sliding reception of a pin 166d therein. Pin 166d is also received within an opening 140d of drive channel 140 and slidably received within a first slot 104d of upper housing 104a such that as drive channel 140 translates relative to upper housing 104a, pin 166d also translates relative to upper housing 104a along first slot 104d. Because first linkage arm 166 is pivotally secured to upper housing 104a, pin 166d travels along cam slot 166c to cam first linkage arm 166 during translation of drive channel 140 relative to upper housing 104a, as will be described in more detail below.

Second linkage arm 168 is pivotally or rotatably secured to pusher bar 160 by a pin 168b received through openings 168c of second linkage arm 168. Pin 168b is also slidably received within a second slot 104e of upper housing 104a such that as first linkage arm 166 is cammed during translation of drive channel 140, second linkage arm 168 is rotated and translated by first linkage arm to translate pusher bar 160, as will be described in more detail below.

As seen in FIGS. 3, 20-21, and 43-44, clip applier 100 further includes a clip carrier 170 disposed within channel assembly 108 and beneath pusher bar 160. Clip carrier 170 is a generally box-like structure having an upper wall 170a, a pair of side walls 170b and a lower wall 170c defining a channel 170d therethrough.

A stack of surgical clips "C" is loaded and/or retained within channel 170d of clip carrier 170 in a manner so as to slide therewithin and/or therealong. The clips of the plurality of surgical clips "C" are arranged in tip-to-tail fashion within channel 170d. Clip carrier 170 further includes a tab 170e (FIG. 21) at a distal end of channel 170d for maintaining the distal most clip "C1" in place and a pair of angled arms 170f dimensioned for engagement against arms 162g of shuttle box 162 when shuttle box 162 is docked with clip carrier 170 to assist in ensuring proper docking between shuttle box 162 and clip carrier 170. Clip carrier 170 further includes a window or slot 170g (FIG. 44) extending through lower wall 170d and configured for the reception of tongue 140e of clip loader 140c therethrough during translation of drive channel 140 relative to clip carrier 170, as will be described in more detail below.

As seen in FIGS. 3 and 23-24, clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. Clip follower 174 is biased against the stack of clips "C" by a clip spring 176. A distal end 176a of clip spring 176 is fixedly attached to jaw assembly 110 at a proximal end thereof (or other fixed structure in the device) and is wound around a spool 176b attached to the proximal end of clip follower 174. During actuation of clip applier 100, as clips "C" are used and the number of clips "C" remaining in clip carrier 100 is reduced, with distal end 176a of spring 176 fixedly secured in place, spring 176 winds-up around spool 176b to urge clip follower against the stack of clips "C" and bias the stack of clips "C" within clip carrier 170. Spring 176 may take the form of a constant force spring or other comparable biasing element.

As seen in FIGS. 3, 12, 14-15, and 22 clip applier 100 includes a drive channel 140 reciprocally supported in and extending between handle assembly 102 and channel assembly 108. A mid portion of drive channel 140 is supported between upper and lower housing halves 104a, 104b of inner housing 104 and a distal end of drive channel 140 is supported between cartridge cover 130 and outer channel 132 of channel assembly 108, at a location below pusher bar 160. A distal end of drive channel 140 is a substantially box-shaped channel 140b for receiving jaw assembly 110 and for actuating jaw assembly 110 upon translation of drive channel 140 relative to jaw assembly 110. Drive channel 140 extends proximally from inner housing 104 and includes an opening 140a for receiving drive pin 124 therethrough for attachment of link members 122 to drive channel 140. Drive channel 140 includes a slot 140g for the reception of first linkage arm 166 therethrough.

Referring now to FIGS. 3, 22, 42 and 44, clip applier 100 further includes a clip loader 140c (FIG. 22) attached to drive channel 140 adjacent a window 140d of drive channel 140 and including a tongue 140e disposed over window 140d and biased outward against clip carrier 170. Tongue 140e is initially disposed in window 140d of drive channel 140 and is configured to extend through a slot 170g of clip carrier 170 to engage the distal most clip "C1" upon translation of drive channel 140 relative to clip carrier 170 to drive distal most clip "C1" into shuttle box 162d, as will be described in further detail below.

Figure 43:
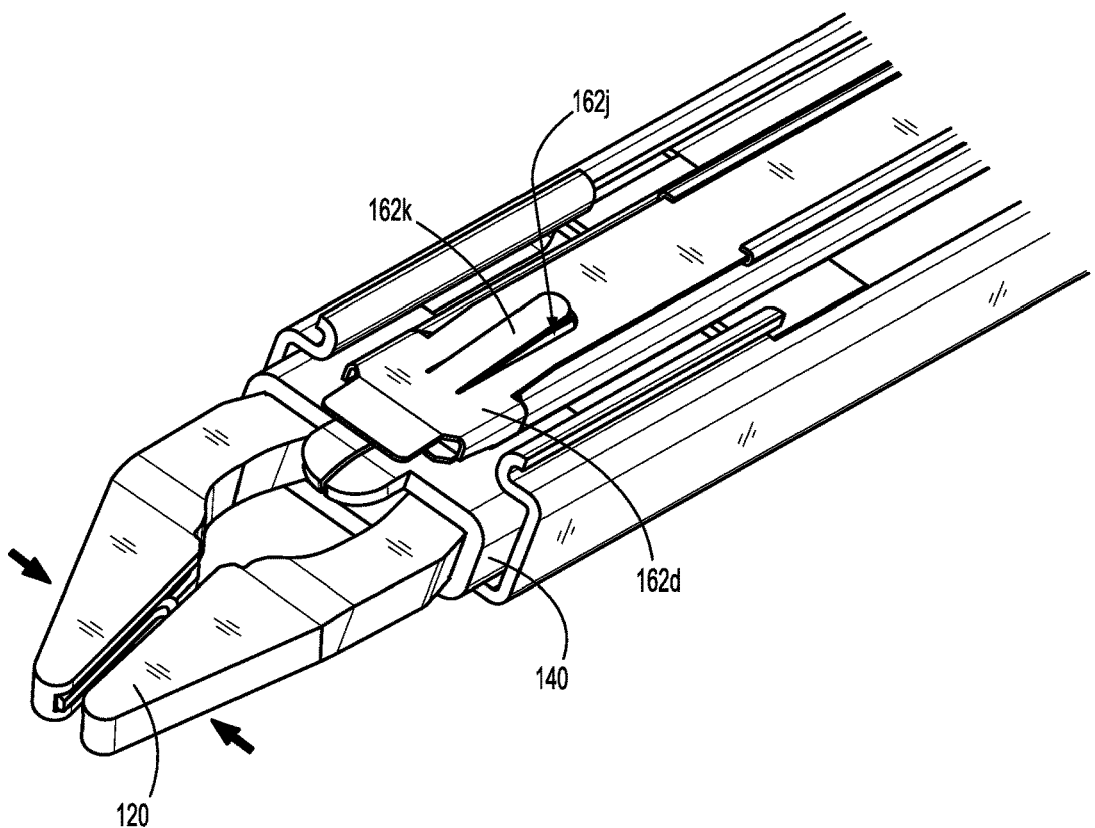
FIG. 43 is a top, perspective view of the jaw assembly and shaft assembly of FIG. 42.

As seen in FIGS. 3, 22, and 43, jaw assembly 110 includes a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of drive channel 140 via a clip 120b or the like extending through a slot 140f of drive channel 140 such that jaws 120 are longitudinally stationary relative to outer channel 132 and drive channel 140. As seen in FIGS. 12, 14, 17 and 19, jaws 120 define a channel 120a therebetween for receipt of a surgical clip "C" therein.

Surgical clip applier 100 may include a lockout mechanism (not shown) disposed in channel assembly 108. The lockout may be actuated by clip follower 174 when a proximal most or final clip "C3" is expelled from the clip applier. The lockout may be urged by clip follower 174 to extend across a path of drive channel 140, thereby preventing drive channel 140 from moving distally. Examples of a variety of suitable lockout mechanisms can be found in U.S. Patent Publication No. 2010/0049216, filed on Aug. 13, 2009, entitled "Surgical Clip Applier and Method of Assembly," the entirety of which is incorporated herein by reference.

Surgical clip applier 100 may further include a counter mechanism (not shown) supported in at least one of the inner housing 104 and the channel assembly 108. The counter mechanism may be configured and adapted to display a change in the clip applier, e.g., increment or decrement, upon each actuation of handles 106. An example of a suitable counter mechanism can be found in U.S. Patent Publication No. 2010/0049216, filed on Aug. 13, 2009, entitled "Surgical Clip Applier and Method of Assembly,", the entirety of which is incorporated herein by reference.

Surgical clip applier 100 may further include a ratchet mechanism (not shown) including a rack having a plurality of teeth and a pawl having at least one tooth and configured to selectively engage the rack. The ratchet mechanism may be configured to inhibit inadvertent return of the drive channel 140 before full actuation of the handles 106. An example of a suitable ratchet mechanism can be found in U.S. Patent Publication No. 2010/0049216, filed on Aug. 13, 2009, entitled "Surgical Clip Applier and Method of Assembly,", the entirety of which is incorporated herein by reference.

With reference to FIGS. 12-57, the operation of the clip applier 100 is provided. Referring now to FIGS. 12-34, prior to any initial squeezing of handles 106 of clip applier 100, in an initial or original position with a first of clips "C" loaded into the jaws 120, the drive pin 124 (FIGS. 25 and 26) and drive channel 140 are located in a proximal-most position with pin 166d at a proximal end of first slot 104d (FIG. 11) of upper housing 104a, pusher bar 160 is located in a distal-most position with pin 168b disposed at a distal end of second slot 104e (FIG. 11) of upper housing 104a, and shuttle bar 162 is located in a distal-most position with pin 162e disposed in cutout 104h (FIG. 11).

Figure 25:
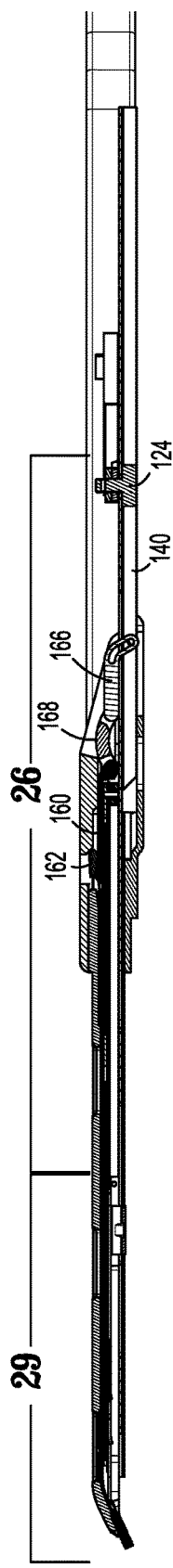
FIG. 25 is a side, cross-sectional view of the clip applier of FIG. 12, as taken along 25-25 of FIG. 1.
Figure 26:
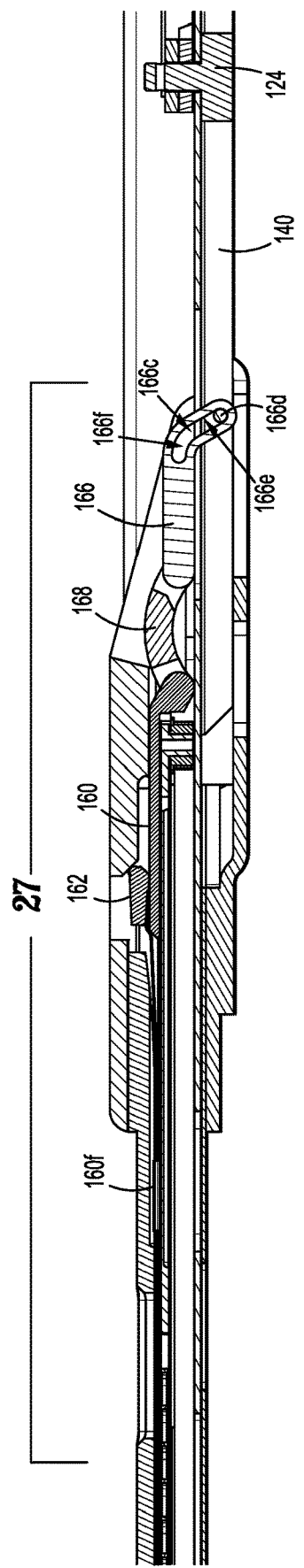
FIG. 26 is an enlarged view of the indicated area of detail of FIG. 25.
Figure 29:
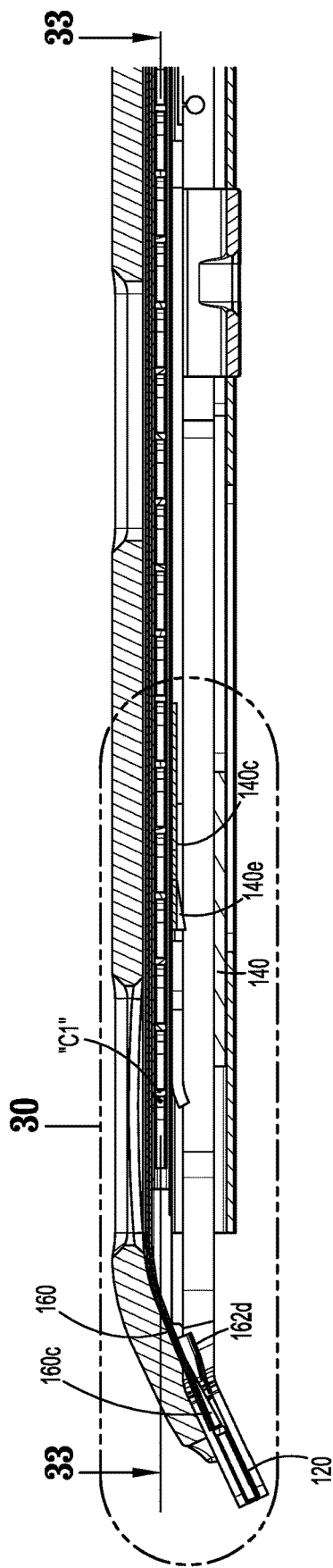
FIG. 29 is an enlarged view of the indicated area of detail of FIG. 25.
Figure 30:
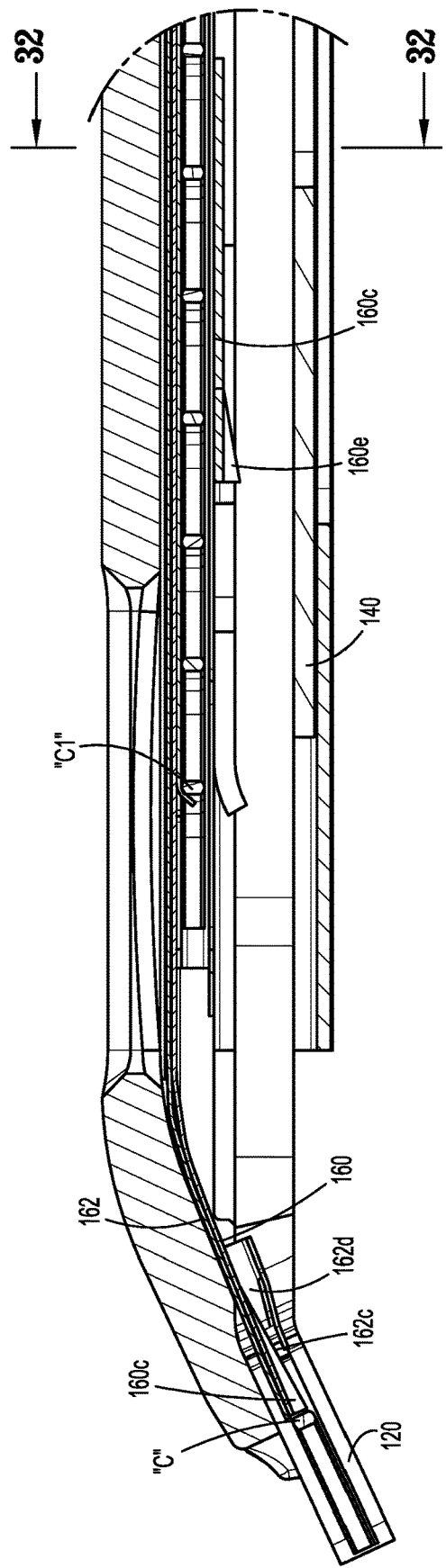
FIG. 30 is an enlarged view of the indicated area of detail of FIG. 29.
Figure 31:
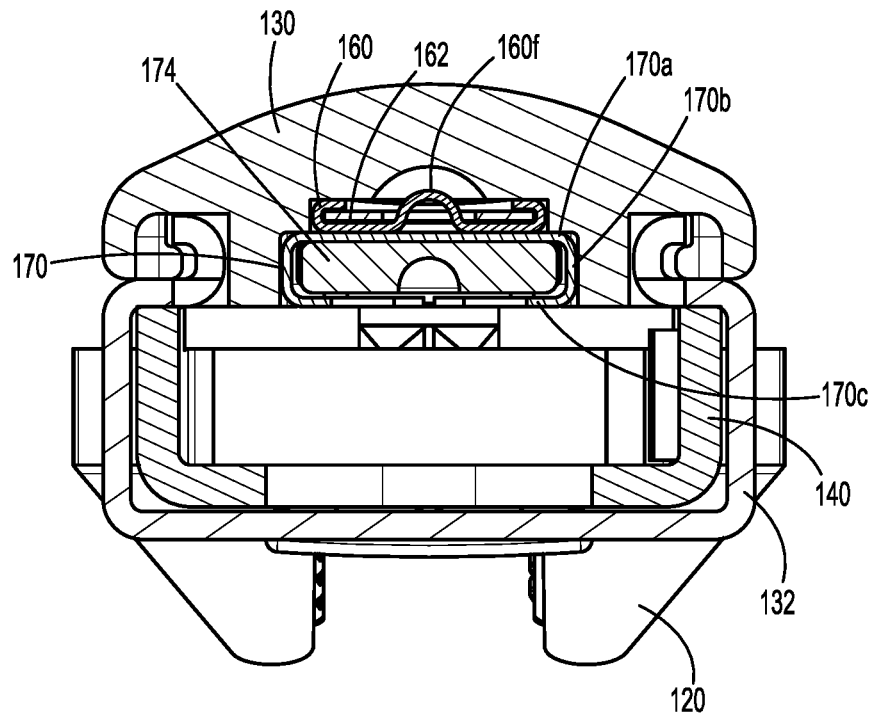
FIG. 31 is cross-sectional view of the shaft assembly as viewed along 31-31 of FIG. 28.
Figure 32:
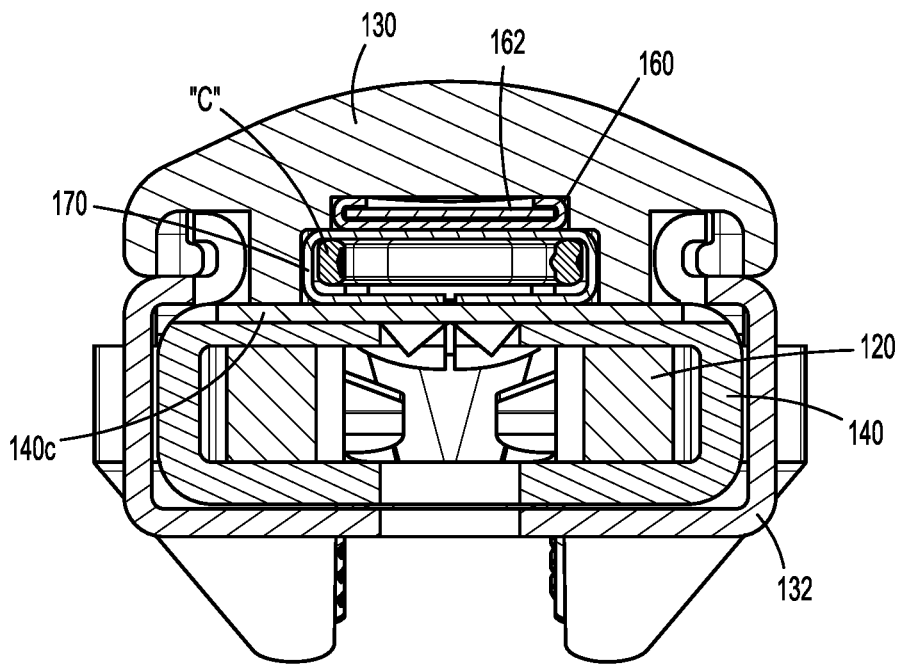
FIG. 32 is cross-sectional view of the shaft assembly as viewed along 32-32 of FIG. 30.
Figure 33:
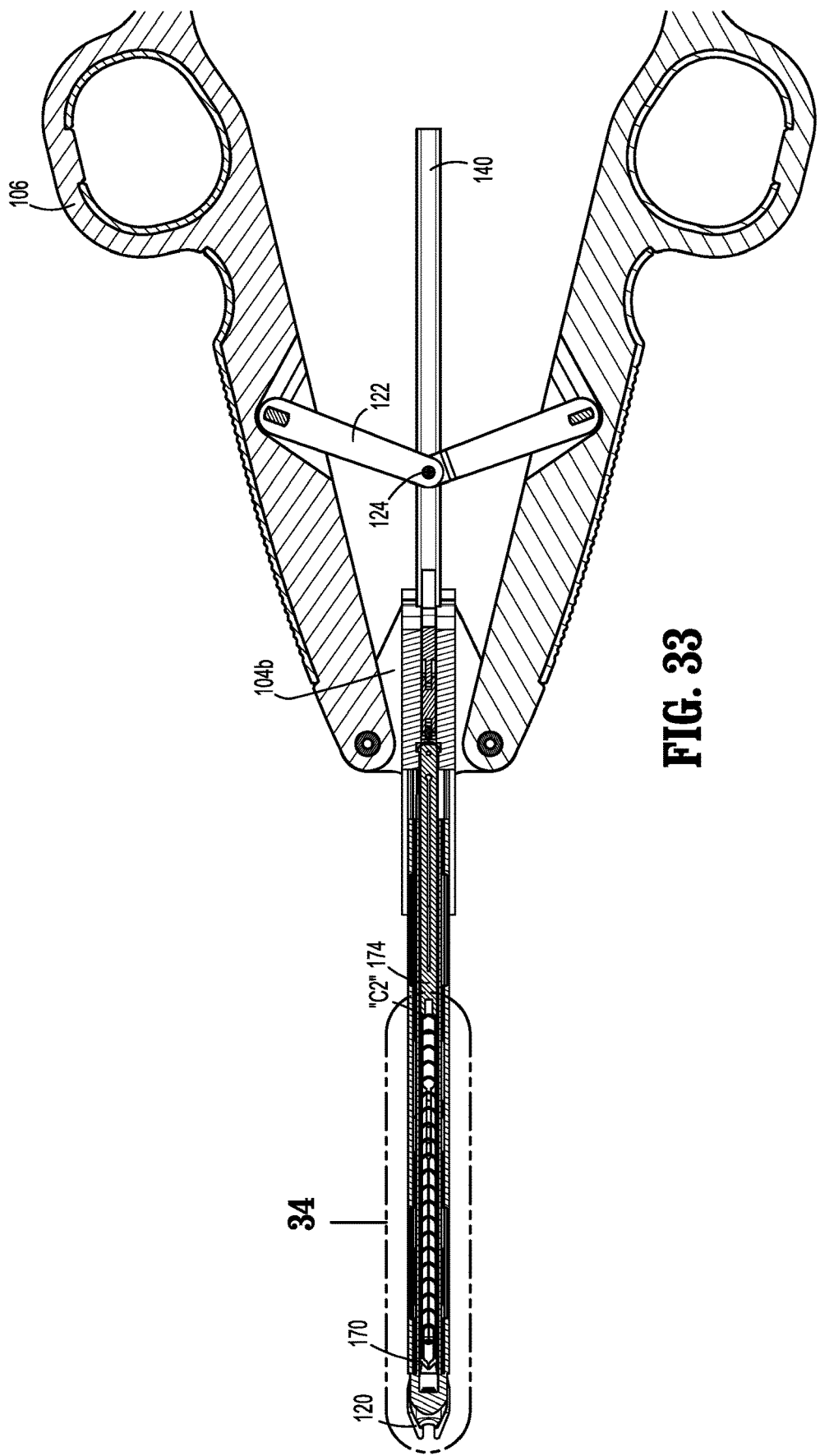
FIG. 33 is cross-sectional view of the shaft assembly as viewed along 33-33 of FIG. 29.
Figure 34:
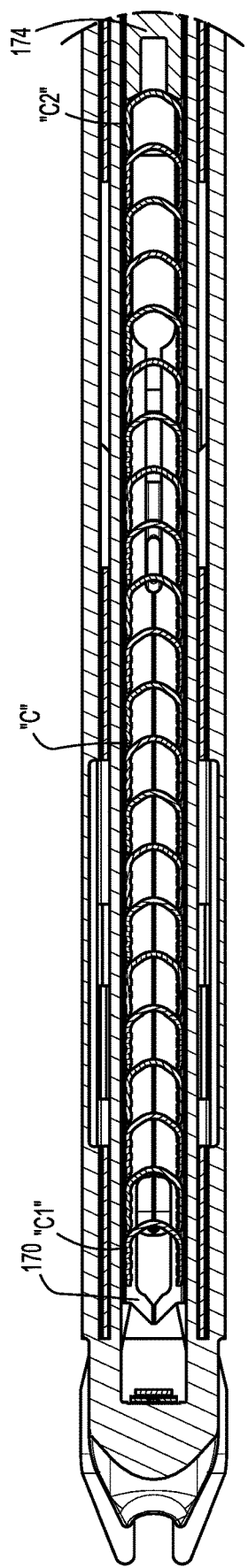
FIG. 34 is an enlarged view of the indicated area of detail of FIG. 33.

As illustrated in FIGS. 25-27, in the initial position, first linkage arm 166 and second linkage arm 168 are substantially longitudinally aligned and fully extended. As illustrated in FIGS. 14-15 and 28, in the initial position, fin 160f of pusher bar 160 is located at a distal end of slot 162f of shuttle bar 162. As seen in FIGS. 16, 17, and 29-30, in the initial position, with pusher 160c of pusher bar 160 positioned against a clip "C" disposed between the jaws 120, shuttle box 162d is docked against and between jaws 120, specifically with wedge 162c disposed between jaws 120 to maintain jaws 120 in a spaced apart condition. As seen in FIGS. 18-19 and 29-30, in the initial position, pusher 160c of pusher bar 160 is engaged against a backspan of a clip "C" loaded into jaws 120. As seen in FIGS. 23 and 24, in the initial position, clip follower 172 is biased against the proximal most clip "C2" with the distal most clip "C1" in clip carrier 170 being maintained in position by tab 170e (FIG. 21) of clip applier 170 until clip loader 140c (FIG. 22) of drive channel 140 loads the distal most clip "C1" from clip carrier 170 into the shuttle box 162d, as will be described in further detail below.

Figure 35:
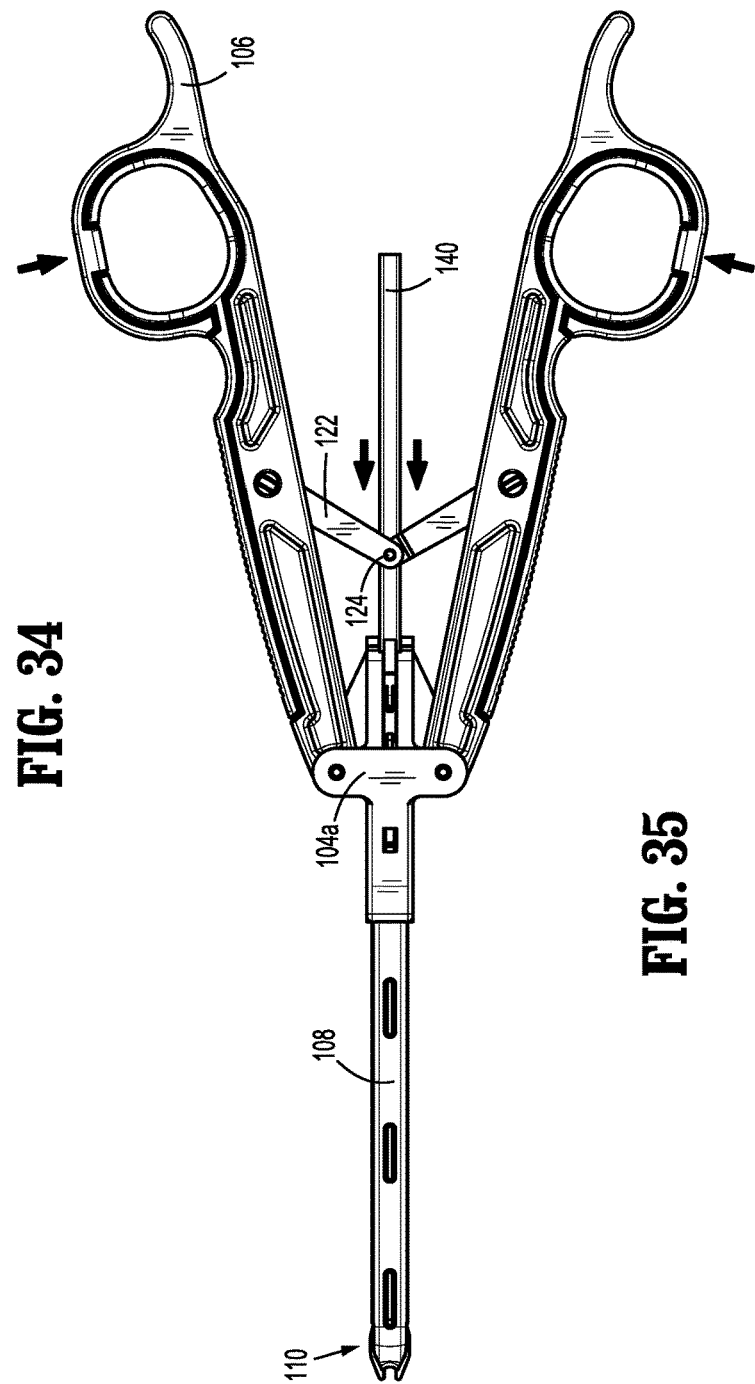
FIG. 35 is a top, plan view of the surgical clip applier of FIG. 1 during an initial squeezing of the handles.

Referring now to FIGS. 35-39, an initial squeezing of handles 106 of clip applier 100 will be described. As illustrated in FIG. 35, as handles 106 are squeezed an initial amount, link members 122 push drive pin 124 distally. As drive pin 124 is pushed distally, drive channel 140 is also translated distally.

As illustrated in FIGS. 36 and 37, during the initial squeezing of handles 106, as drive channel translates distally, pin 166d of linkage mechanism 164 also moves distally along slot 104d (FIG. 11) of upper housing 104a due to the disposition of pin 166d through opening 140d (FIG. 3) of drive channel 140.

During the initial squeezing of handles 106, as pin 166d moves distally along slot 104d, pin 166d cams along a cam portion 166f (FIG. 37) of cam slot 166c of first linkage arm 166 to rotate first linkage arm 166 about protrusions 166b (FIG. 11) disposed in opening 104g (FIG. 11) of upper housing 104a.

As first linkage arm 166 rotates about protrusions 166b, second linkage arm 168 rotates relative to first linkage arm 166 about protrusions 166a of first linkage arm 166 due to the disposition of protrusions 166a (FIGS. 3 and 11) in openings 168a (FIGS. 3, 11, 14 and 15) of second linkage arm 168. As second linkage arm 168 rotates about protrusions 166a (FIGS. 3 and 11) of first linkage arm 166, pin 168b (FIG. 37) slides proximally along slot 104e of upper housing 104a.

During the initial squeezing of handles 106, as pin 168b slides proximally along slot 104e, pusher bar 160 is also pulled proximally due to the disposition of pin 168b in openings 160d (FIGS. 3 and 11) of pusher bar 160.

As pusher bar 160 is pulled proximally by pin 168b, raised portion 160g of pusher bar 160 is moved proximal of shuttle bar 162 to allow legs 162e of shuttle bar 162 to disengage from cutout 104h of upper housing 104a.

Referring now to FIG. 38, during the initial squeezing of handles 106, as pusher bar 160 is pulled proximally by pin 168b, fin 160f of pusher bar 160 slides along slot 162f of shuttle bar 162 and engages against a proximal end of slot 162f. Once fin 160f of pusher bar 160 engages against the proximal end of slot 162f, and pin 162e of shuttle bar 162 disengage from cutout 104h of upper housing 104a, shuttle bar 162 also begins to move proximally with pusher bar 160 due to the engagement of fin 160f with the proximal end of slot 162f.

Referring now to FIG. 39, as pusher bar 160 moves proximally, the pusher 160c disengages from the clip "C" disposed in the jaws 120 and moves proximally out of jaws 120.

As pusher bar 160 begins to move shuttle bar 162 proximally, shuttle box 162d is also moved proximally with wedge 162c of shuttle bar 162 being retracted from between jaws 120.

Also during the initial squeezing of handles 106, as drive channel 140 moves distally, clip loader 140c also moves distally.

Figure 41:
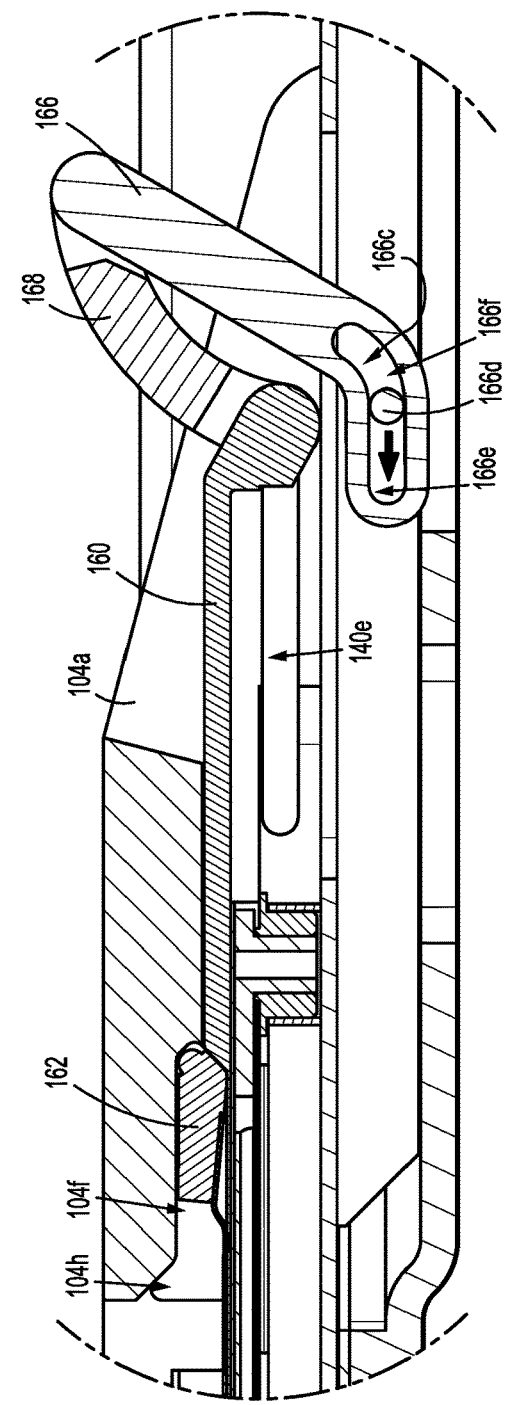
FIG. 41 is an enlarged view of the indicated area of detail of FIG. 40.

Referring now to FIGS. 40-44, a further continued squeezing of handles 106 of clip applier 100 will be described. As illustrated in FIGS. 40 and 41, as handles 106 (FIG. 1) are squeezed a subsequent amount, drive channel 140 continues to move distally with pin 166d of linkage mechanism 164 continuing to travel along slot 104d (FIG. 11) of upper housing 104a and along a cam portion 166f of cam slot 166c to further rotate first linkage arm 166 to a maximal rotation position (FIG. 41) relative to upper housing 104a. As seen in FIG. 41, cam slot 166c includes a cam portion 166f defining a curved or arcuate path and a dwell portion 166e defining a substantially linear path that is substantially aligned with drive channel 140 when first linkage arm 166 is at the maximal rotation position. Dwell portion 166e is configured to allow further distal movement of pin 166d of linkage mechanism 164 along slot 104d of upper housing 104a and cam slot 166c of first linkage arm 166 due to the further distal translation of drive channel 140 without requiring further rotation of first linkage arm 166 relative to upper housing 104a.

As first linkage arm 166 rotates to the maximal rotation position (FIG. 41) relative to upper housing 106a, during the further continued squeezing of handles 106, second linkage arm 168 also rotates relative to first linkage arm 166. As second linkage arm 168 rotates relative to first linkage arm 166, pin 168b of second linkage arm 168 continues to move proximally along slot 104e of upper housing 104a until pin 168b reaches a proximal end of slot 104e (FIG. 41).

As pin 168b of second linkage arm 168 continues to move proximally along slot 104e, during the further continued squeezing of handles 106, pusher bar 160 also continues to move proximally due to the disposition of pin 168b in openings 160d of pusher bar 160 until pin 168b reaches the proximal end of slot 104e. Once pin 168b reaches the proximal end of slot 104e, pusher bar 160 is disposed in a proximal most position.

During the further continued squeezing of handles 106, as pusher bar 160 continues to move proximally, with fin 160f engaged against the proximal end of slot 162f of shuttle bar 162, shuttle bar 162 also continues to move proximally. When pusher bar reaches the proximal most position, shuttle bar 162, which is pulled proximally by fin 160f, also reaches a proximal most position at a proximal end of groove 104f of upper housing 104a.

Further, once pin 166d reaches the dwell portion 166e of first linkage arm 166, with pusher bar 160 and shuttle bar 162 in the proximal most positions, any further squeezing of handles 106 continues distal translation of drive bar 140 and pin 166d distally along slot 104d of upper housing 104a and along dwell portion 166e of cam slot 166c without further moving pusher bar 160 and shuttle bar 162 proximally.

Figure 42:
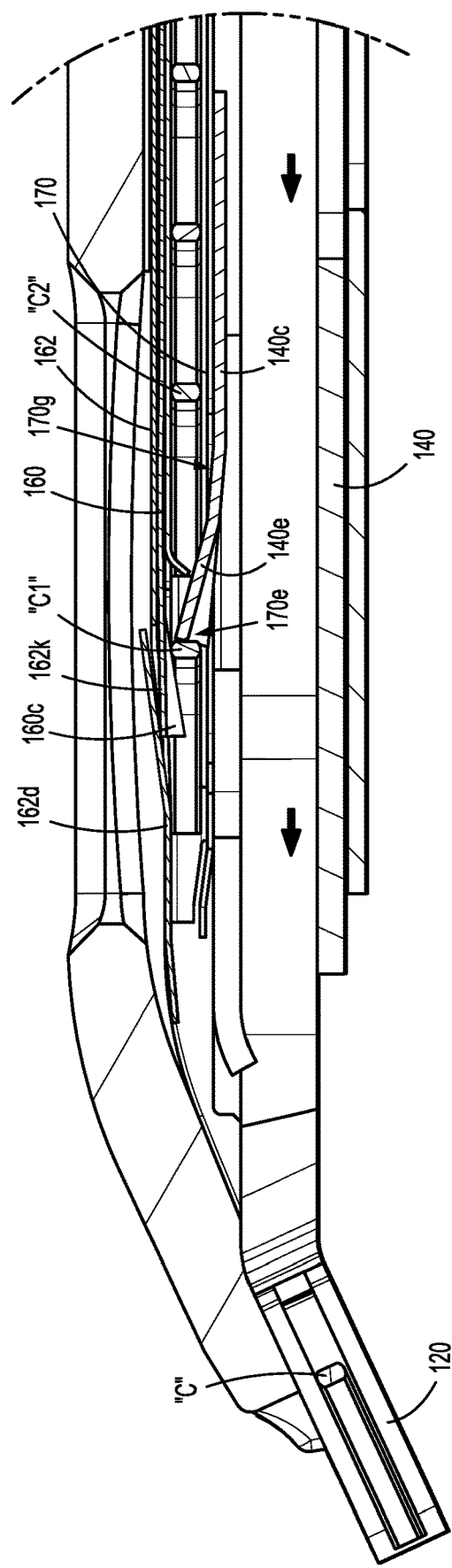
FIG. 42 is an enlarged view of the indicated area of detail of FIG. 40.
Figure 44:
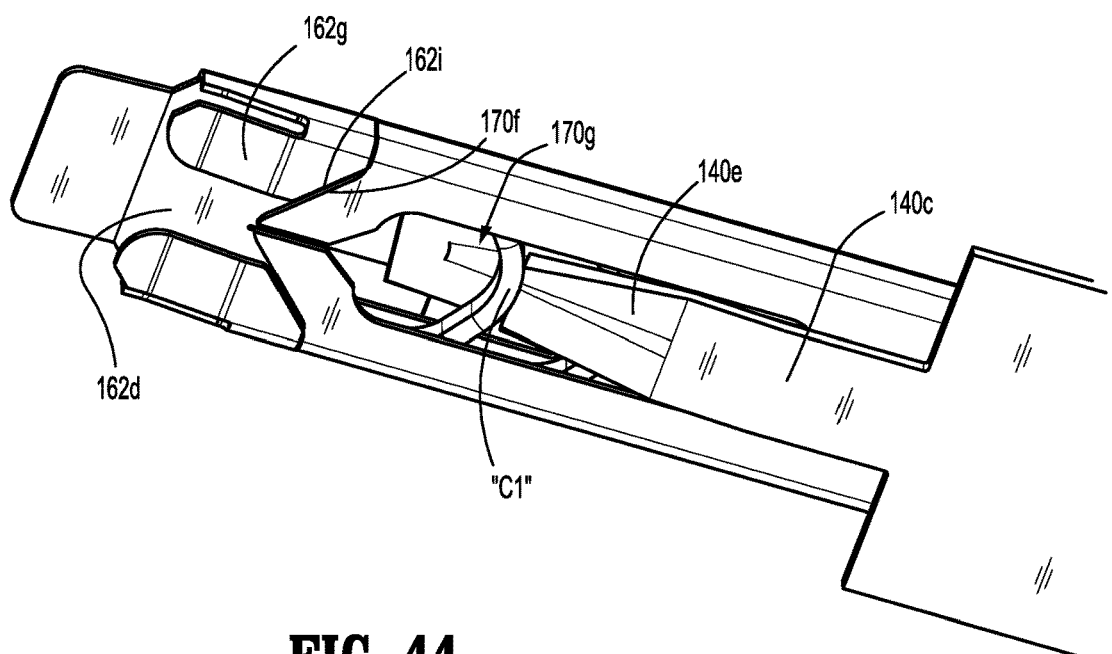
FIG. 44 is a bottom, perspective view of the shaft assembly FIG. 43, with the jaw assembly, drive channel, and lower cartridge removed therefrom.

Referring now to FIGS. 42-44, during the further continued squeezing of handles 106, when shuttle bar 162 reaches the proximal most position, shuttle box 162d is also disposed at a proximal most position docked against a distal end of clip carrier 170.

During the further continued squeezing of handles 106, when pusher bar 160 and shuttle bar 162 are in the proximal most positions, pusher 160c of pusher bar 160 is received in cutout 162j of shuttle box 162d with flexible tab 162k of shuttle box 162d flexing to provide clearance for pusher 160c.

As drive channel 140 continues to move distally, clip loader 140c also moves distally with tongue 140e extending through slot 170g of clip carrier 170 to engage a backspan of the distal most clip "C1" to urge the distal most clip "C1" into the shuttle box 162d.

During the further continued squeezing of handles 106, as drive channel 140 is translated distally, a surface of drive channel 140 engages against a surface of jaws 120 to cam jaws 120 from an open position to a closed position to form a clip "C" disposed between the jaws 120.

Referring now to FIGS. 45-50, the state of clip applier 100 with handles 106 in the fully squeezed position will now be described.

As illustrated in FIGS. 45-47, with handles 106 in the fully squeezed position, drive channel 140 is at a distal most position camming jaws 120 closed to form a clip "C" about tissue or a vessel "T" (FIG. 47).

Figure 48:
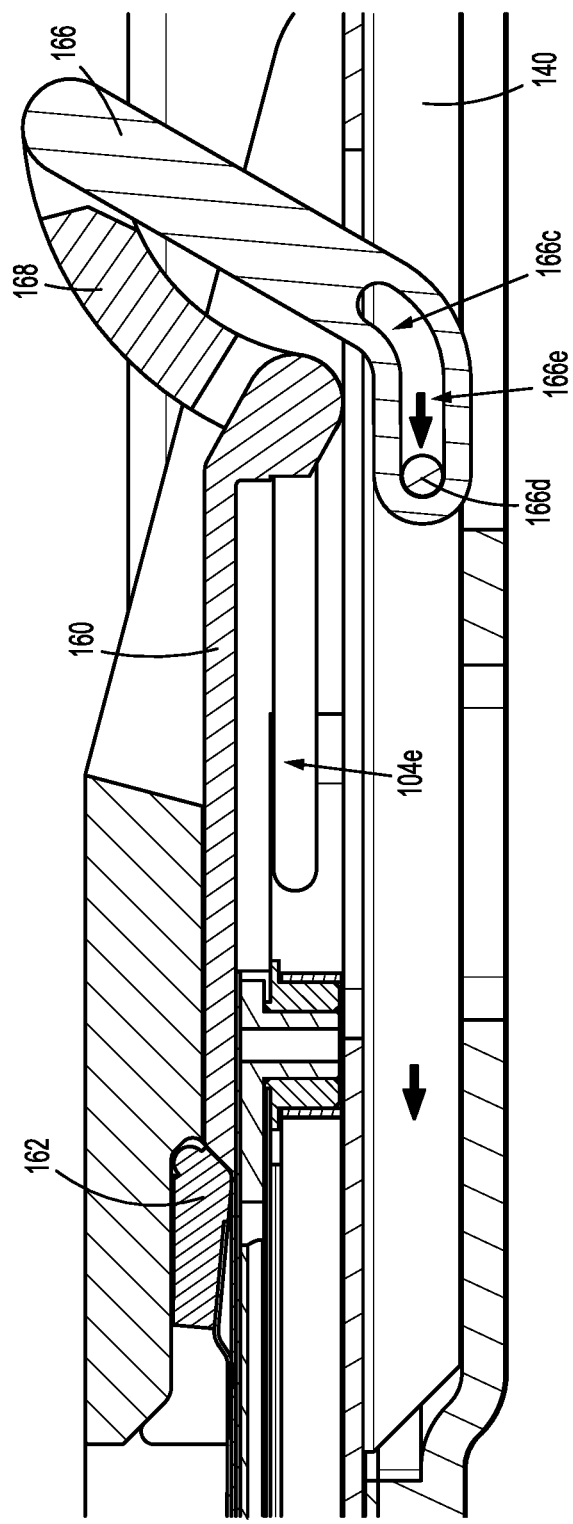
FIG. 48 is another enlarged view of the area indicated as 41 in FIG. 40, now with the handle in the fully squeezed condition.

Referring now to FIG. 48, drive channel 140 is at the distal most position with pin 166d at a distal end of slot 104d of upper housing 104a and at the end of dwell portion 166e of cam slot 166c. Pusher bar 160 and shuttle bar 162 are still disposed at the most proximal positions.

Figure 49:
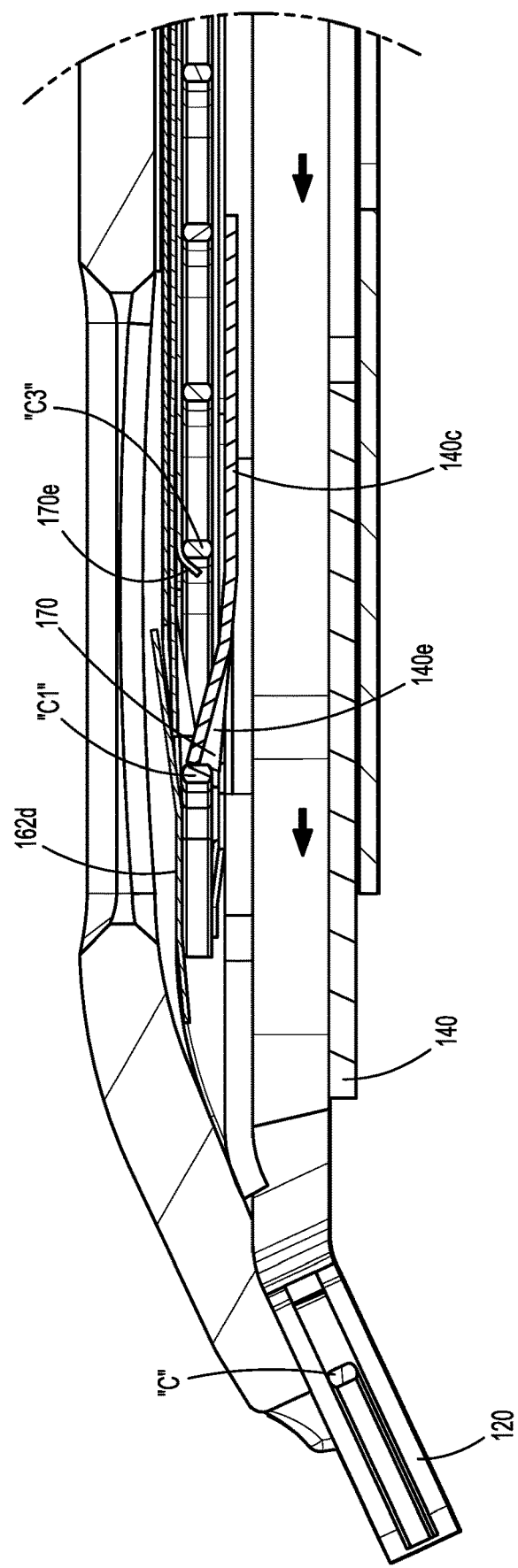
FIG. 49 is an enlarged, cross-sectional view of the distal end of the shaft assembly and the jaw assembly of FIG. 45.
Figure 50:
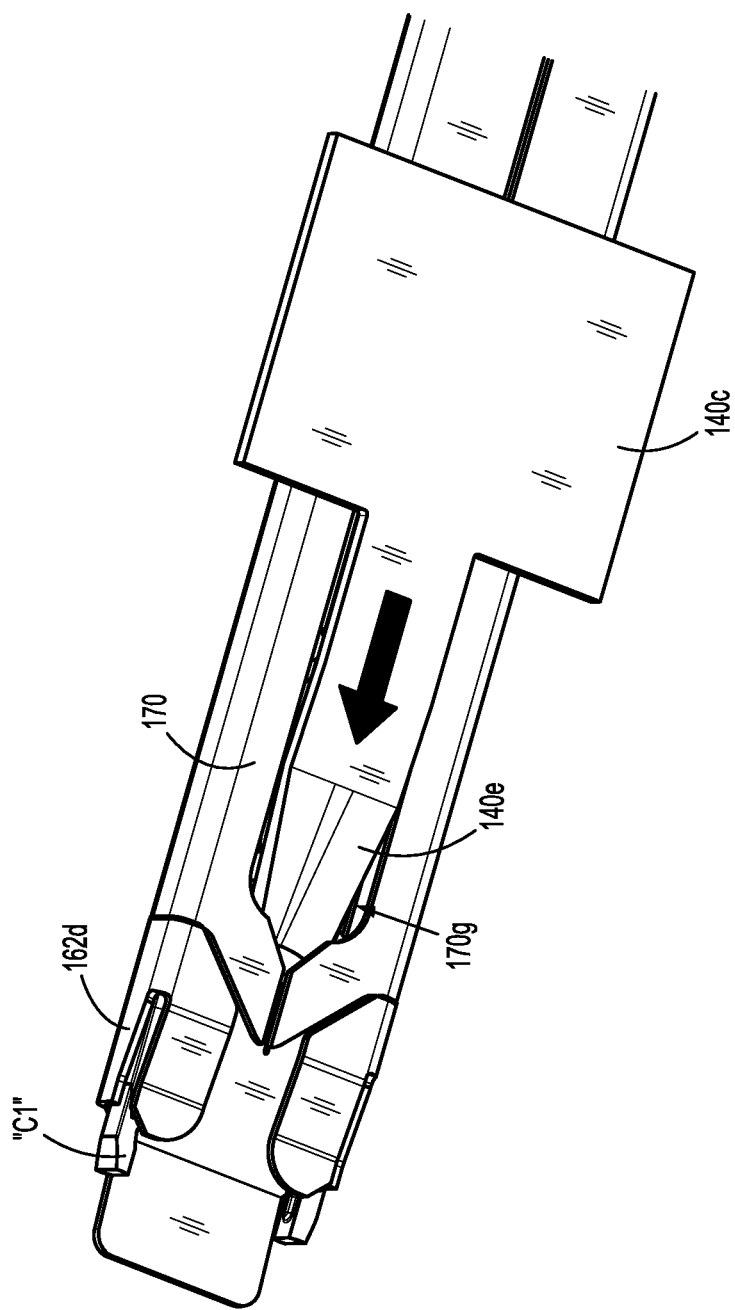
FIG. 50 is an enlarged, perspective view of the distal end of the shaft assembly of FIG. 45, with parts removed, illustrating the clip loader driving the distal most clip into the shuttle box.

Referring now to FIGS. 49 and 50, with handles 106 in the fully squeezed position and drive channel 140 in the distal most position, tongue 140e of clip loader 140c is fully inserted and extending through slot 170g of clip carrier 170 with the distal most clip "C1" of the stack of clips "C" fully urged into shuttle box 162d. A next distal most clip "C3" is retained within clip carrier 170 under the bias of spring 176 due to tab 170e.

Referring now to FIGS. 51-57, the un-squeezing or return of handles 106 of clip applier 100 to the original position will now be described.

Figure 51:
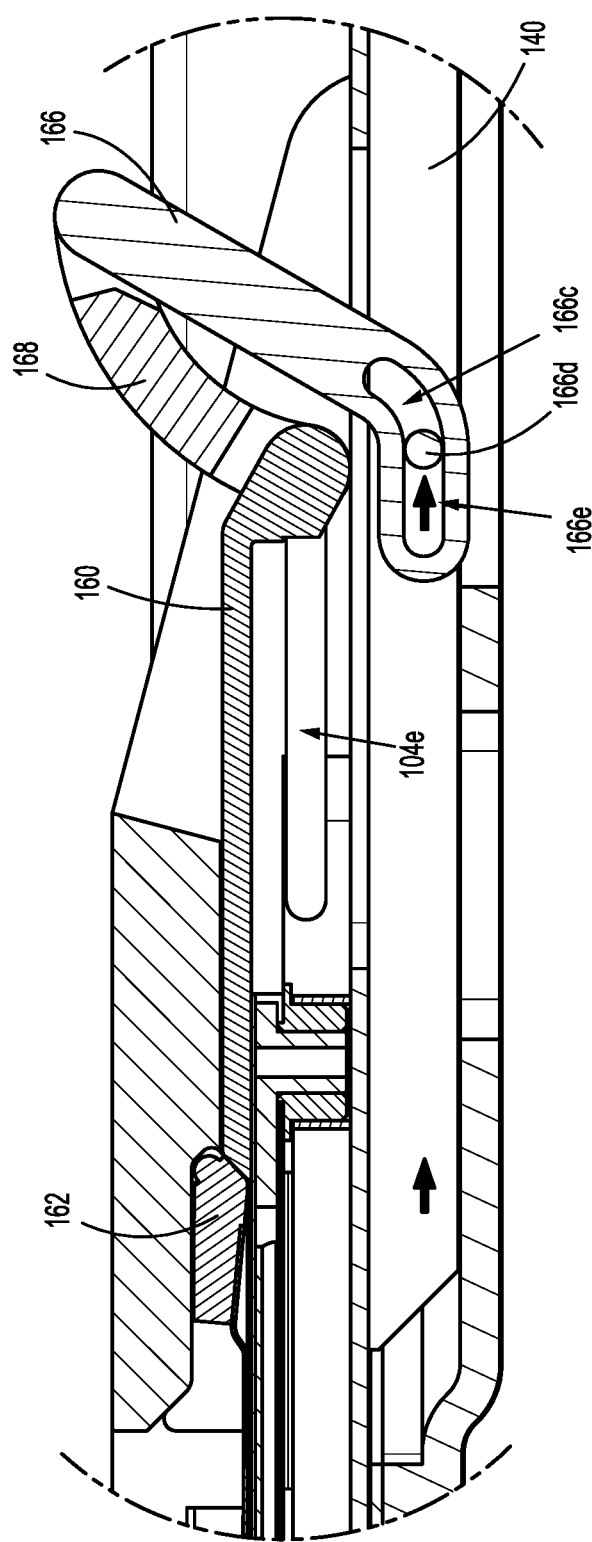
FIG. 51 is another enlarged view of the area indicated as 41 in FIG. 40, now with the handle in the initial un-squeezed condition.

As illustrated in FIG. 51, during initial un-squeezing of handles 106, drive channel 140 begins to move proximally from the distal most position due to the engagement of drive pin 124 with link members 122 of handles 106. As drive channel 140 moves proximally an initial amount, pin 166d of linkage mechanism 164 moves along dwell portion 166e of first linkage arm 166 and proximally along slot 104d of upper housing 104a. First and second linkage arms 166 and 168 remain in the maximal rotation position with pusher bar 160 and shuttle bar 162 remaining disposed at the proximal most positions due.

Figure 52:
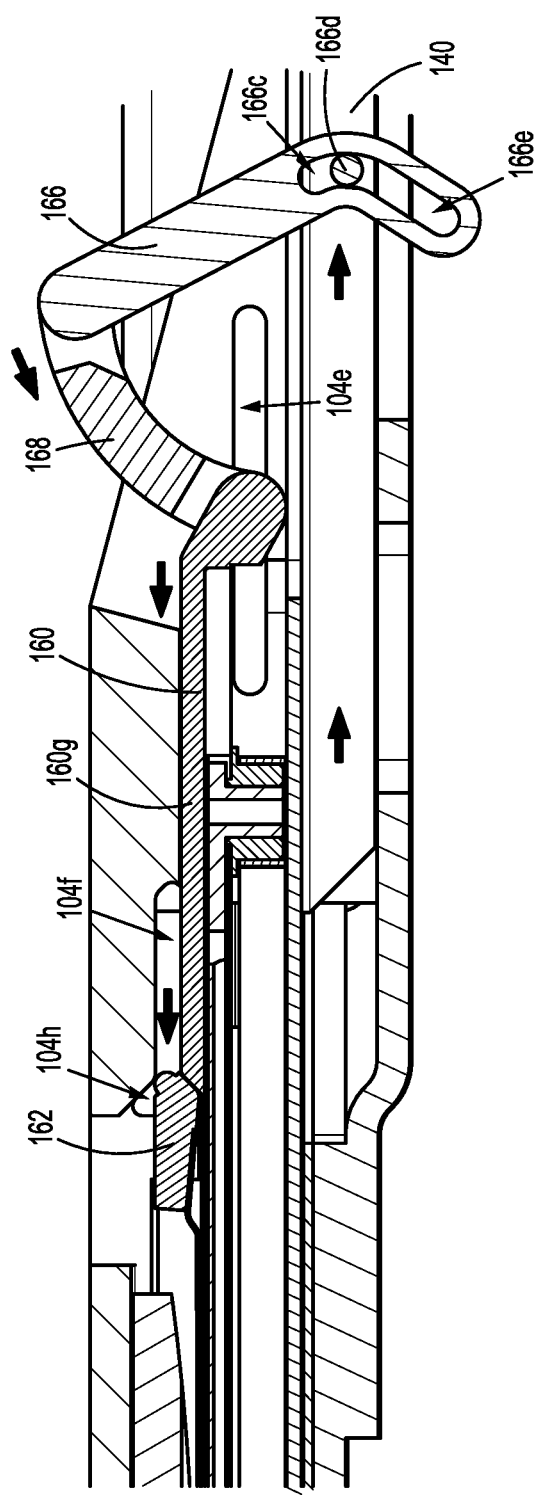
FIG. 52 another enlarged view of the area indicated as 41 in FIG. 40, now with a continued un-squeezing of the handles.

Referring now to FIG. 52, during a further un-squeezing of handles 106 as drive channel 140 and pin 166d continue to translate proximally, pin 166d of linkage mechanism 164 begins to cam against cam slot 166c of first linkage arm 166 to rotate first linkage arm 166 relative to upper housing 104a about protrusions 166b.

As first linkage arm 166 rotates relative to upper housing 104a, second linkage arm 168 rotates relative to first linkage arm 166, due to the disposition of protrusions 166a of first linkage arm 166 in openings 168a of second linkage arm 168, and drives pin 168b of linkage mechanism 164 distally along slot 104e of upper housing 104a.

During the further un-squeezing of handles 106, as pin 168b of linkage mechanism 164 moves distally along slot 104e of upper housing 104a, pusher bar 160 is translated distally due to the disposition of pin 168b of linkage mechanism 164 in openings 160d of pusher bar 160.

As pusher bar 160 translates distally, shuttle bar 162 is also translated distally along groove 104f due to the engagement of raised portion 160g of pusher bar 162 against a proximal end of shuttle bar 162 until shuttle box 162d docks (FIGS. 54 and 55) against jaws 120 in a distal most position. In this manner, distal most clip "C1" is transported, by shuttle box 162d, from clip carrier 170 to jaws 120 in a controlled manner.

Figure 53:
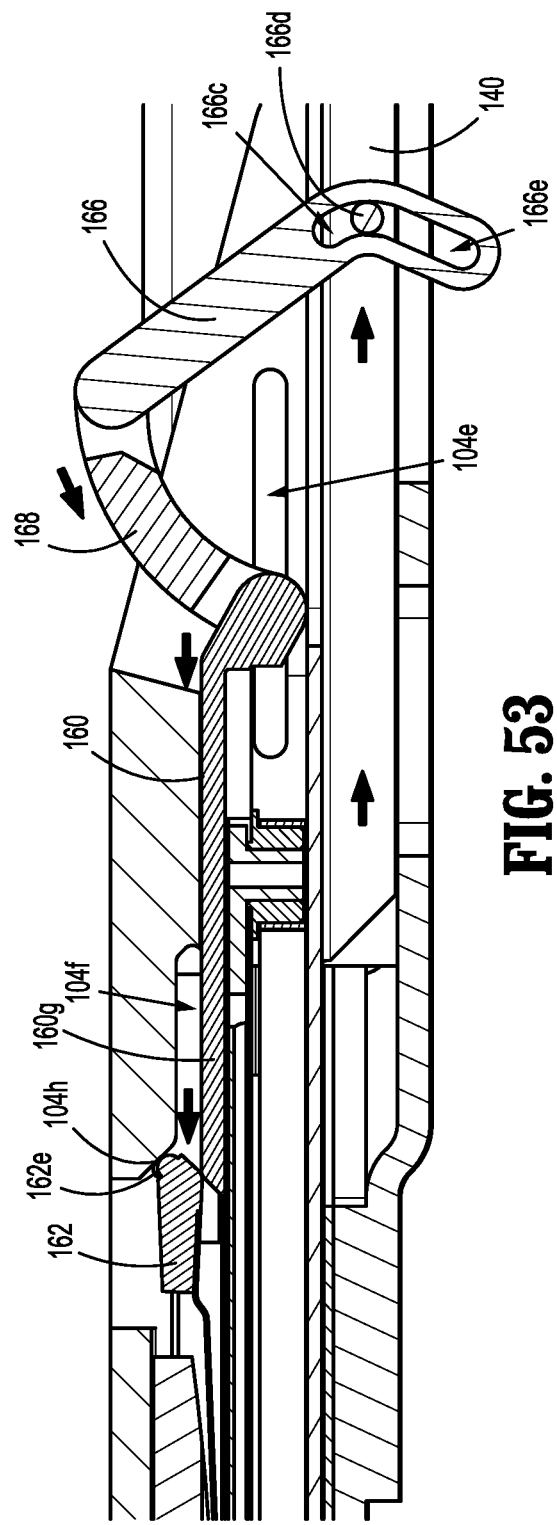
FIG. 53 another enlarged view of the area indicated as 41 in FIG. 40, now with a further continued un-squeezing of the handles.

Referring now to FIG. 53, during yet a further un-squeezing of handles 106, as drive channel 140 and pin 166d of linkage mechanism 164 continue to translate proximally, with pin 166d further rotating first linkage arm 166 relative to upper housing 104a, with first linkage arm 166 further rotating second linkage arm 168 relative to first linkage arm 166, with second linkage arm 168 further driving pin 168b distally along slot 104e of upper housing 104a, and with pin 168b further translating pusher bar 160 distally, raised portion 160g of pusher bar 160 moves under the proximal end of shuttle bar 162 and drives pin 162e of shuttle bar 162 into cutout 104h of upper housing 104a.

Figure 54:
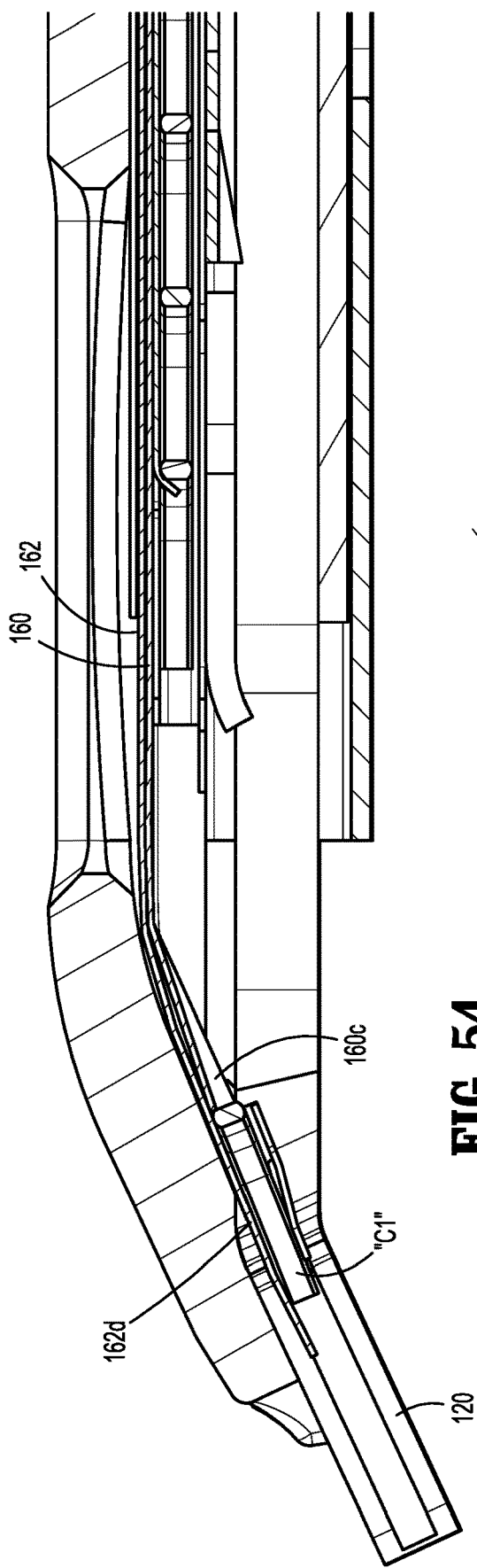
FIG. 54 is a side, cross-sectional view of the distal end of the shaft assembly of FIG. 45, during the continued un-squeezing of the handles.
Figure 55:
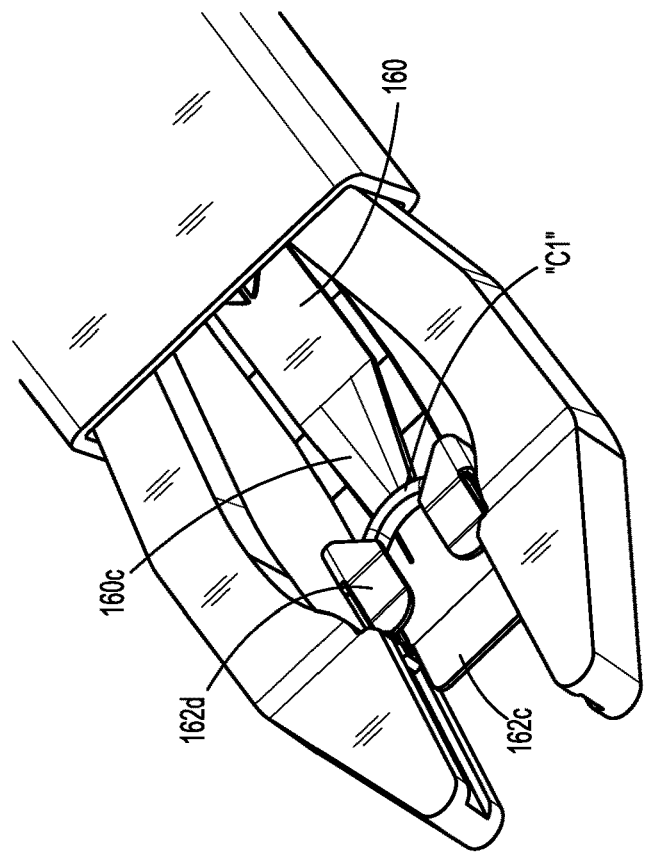
FIG. 55 is a perspective view of the distal end of the shaft assembly and the jaw assembly of FIG. 54.

Referring now to FIGS. 54 and 55, as pusher bar 160 continues to translate distally, with shuttle bar 162 being disposed in the distal most position, pusher 160c translates distally relative to shuttle box 162d to engage the backspan of distal most clip "C1" and urge distal most clip "C1" into the jaws 120. As can be seen in FIGS. 54 and 55, wedge 162c of shuttle bar 162 is disposed between jaws 120 to maintain jaws 120 in an open condition for insertion of distal most clip "C1."

Figure 56:
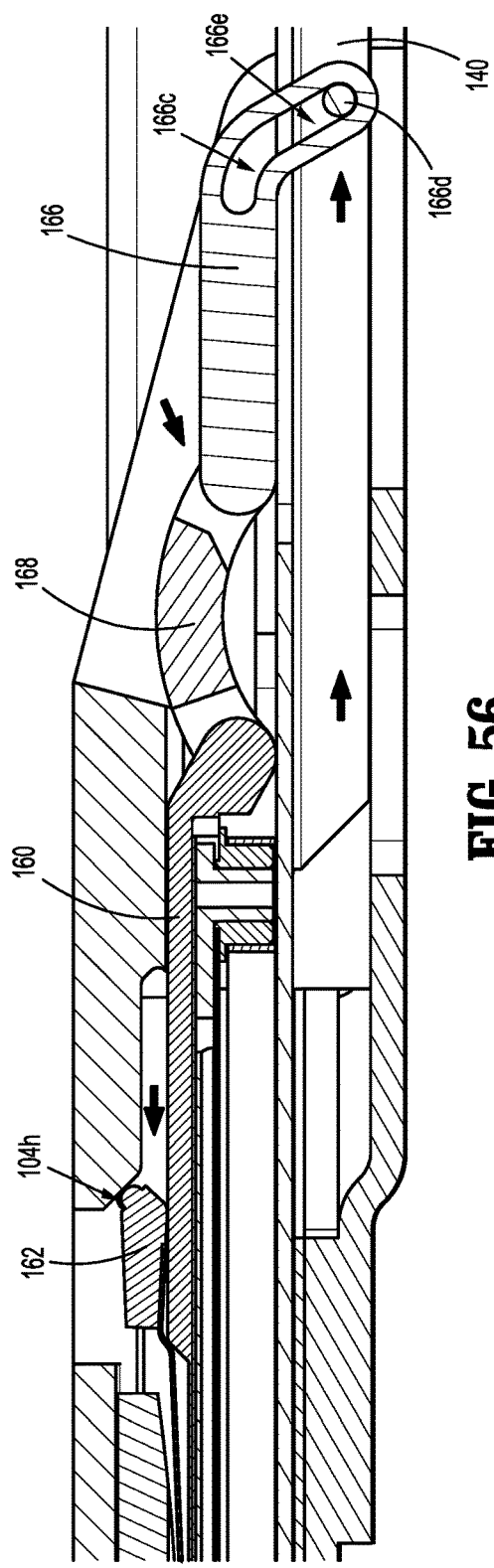
FIG. 56 is another enlarged view of the area indicated as 41 in FIG. 40, now with the handle in the fully un-squeezed condition.

Referring now to FIG. 56, as the handles 106 are fully un-squeezed, with drive channel 140 in the proximal most position, pin 166d of linkage mechanism 164 is at a proximal end of slot 104d of upper housing 104a and disposed at the end of dwell portion 166e having rotated first linkage arm 166 to a position substantially aligned with drive channel 140. Second linkage arm 168 is substantially aligned with drive channel 140 with pin 168b of linkage mechanism 164 disposed at a distal end of slot 104e of upper housing 104a. Pusher bar 160 is disposed at a distal most position with raised portion 160g thereof disposed beneath the proximal end of shuttle bar 162. Pin 162e of shuttle bar 162 is disposed in cutout 104h of upper housing 104a to inhibit proximal movement of shuttle bar 162 relative to upper housing 104a.

Figure 57:
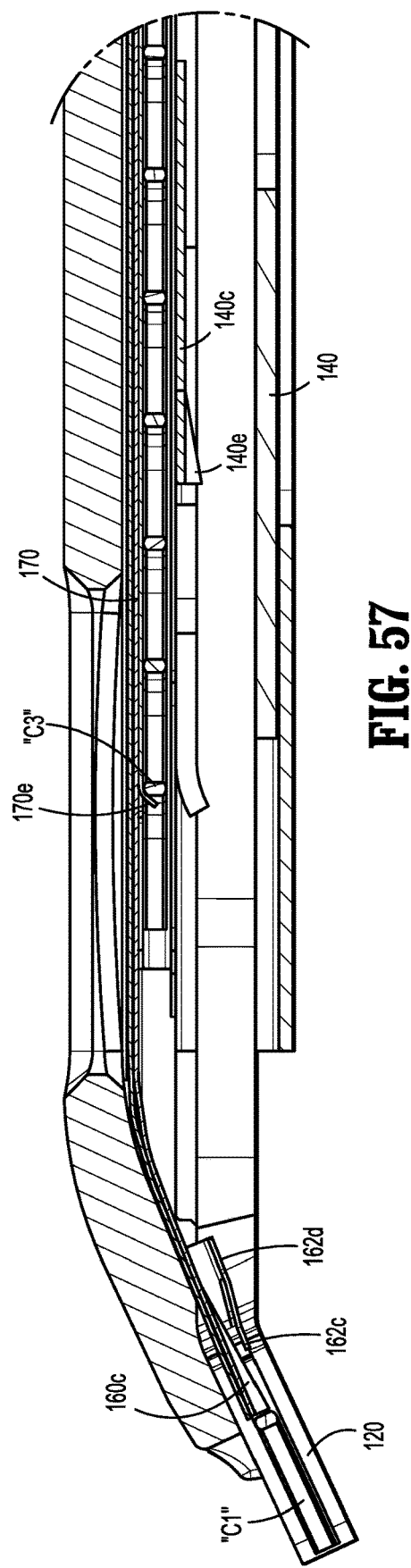
FIG. 57 is a side, cross-sectional view of the distal end of the shaft assembly and the jaw assembly of FIG. 54, after the handles have been fully un-squeezed.

Referring now to FIG. 57, as the handles 106 are fully un-squeezed, shuttle box 162d is docked against jaws 120 with wedge 162c thereof disposed between jaws 120 to maintain jaws 120 in the open condition. Pusher 160c is disposed against the backspan of distal most clip "C1" disposed in jaws 120. With drive channel 140 in the proximal most position, tongue 140e of clip loader 140c is disposed proximal of slot 170g of clip carrier 170. The next distal most clip "C3" is disposed at the distal end of clip carrier 170 and retained by flexible tab 170e of clip carrier 170 and biased by spring 176.

After handles 106 are returned to the initial or original position, clip applier 100 is ready to apply additional clips to tissue.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
   a housing;
   at least one handle movably connected to the housing;
   a channel assembly extending distally from the housing;
   a clip carrier disposed within the channel assembly, the clip carrier configured to slidably retain a plurality of clips therein;
   a jaw assembly including a pair of jaws extending from an end of the channel assembly, opposite the housing, the jaw assembly operable to effect formation of a distal-most clip of the plurality of clips in response to movement of the at least one handle;
   a clip pusher bar slidably supported within at least one of the housing and the channel assembly, the clip pusher bar defining a channel therein; and
   a shuttle bar slidably disposed in the channel of the clip pusher bar, the shuttle bar including a shuttle box configured to receive the distal-most clip of the plurality of clips through a first end portion of the shuttle box, opposite the pair of jaws, for transporting the distal-most clip towards the jaw assembly.

2. The clip carrier according to claim 1, wherein the shuttle box includes a pair of arms defining a slot configured to receive the distal-most clip of the plurality of clips therein.

3. The clip applier according to claim 2, wherein the shuttle bar includes a wedge extending from a second end portion of the shuttle box, opposite the first end portion of the shuttle box, the wedge configured for selective insertion between the pair of jaws to maintain the pair of jaws in an open condition.

4. The clip applier according to claim 2, wherein the shuttle box is configured to transport the distal-most clip from the clip carrier towards the jaw assembly upon distal movement of the shuttle bar.

5. The clip applier according to claim 4, wherein the shuttle box is configured to at least partially surround the distal-most clip within the slot thereof, when the distal-most clip is transported from the clip carrier towards the jaw assembly upon distal movement of the shuttle bar.

6. The clip carrier according to claim 2, wherein the shuttle box includes an angled surface adjacent the first end portion of the shuttle box, and wherein the clip carrier includes at least one angled arm corresponding to the angled surface of the shuttle box.

7. The clip applier according to claim 6, wherein the shuttle box is configured to be docked against the clip carrier when the shuttle bar is in a proximal-most position to receive the distal-most clip therein.

8. The clip applier according to claim 7, wherein when the shuttle box is docked against the clip carrier, a distal end portion of the at least one angled arm of the clip carrier is configured to be positioned between the pair of arms of the shuttle box.

9. The clip applier according to claim 7, wherein when the shuttle box is in the proximal-most position, the shuttle box is configured to be positioned distally of the plurality of clips.

10. The clip applier according to claim 1, wherein the shuttle box is docked against the jaw assembly when the shuttle bar is in a distal-most position.

11. The clip applier according to claim 2, wherein the clip pusher bar is configured to urge the distal-most clip from a location retained in the slot of the shuttle box to a location between the pair of jaws upon distal movement of the clip pusher bar.

12. The clip applier according to claim 2, wherein the clip pusher bar is configured to engage the distal-most clip retained in the slot of the shuttle box, when the shuttle box is spaced-apart from the clip carrier.

13. The clip applier according to claim 2, wherein the clip pusher bar is configured to engage the distal-most clip retained in the slot of the shuttle box, led through the first end portion of the shuttle box, upon distal movement of the clip pusher bar.

14. The clip applier according to claim 13, wherein the shuttle bar includes a flexible tab extending from a surface adjacent the shuttle box, the flexible tab configured to provide clearance during movement of the clip pusher bar relative to the shuttle box.

15. The clip applier according to claim 2, further comprising a clip loader slidably supported within the channel assembly and translatable relative to the clip carrier to urge the distal-most clip disposed within the clip carrier into the shuttle box, led through the first end portion of the shuttle box.

16. The clip applier according to claim 15, wherein the clip carrier includes a slot defined through a lower surface thereof, the slot configured to receive the clip loader when the clip loader translates relative to the clip carrier, wherein a tongue of the clip loader is configured to engage the distal-most clip disposed adjacent the slot of the clip carrier to urge the distal-most clip into the shuttle box.

17. The clip applier according to claim 16, wherein the clip loader is configured to urge the distal-most clip into the slot of the shuttle box, led through the first end portion of the shuttle box, when the shuttle box is abutting the clip carrier.

18. The clip applier according to claim 1, wherein the distal-most clip is configured to be transported from the clip carrier towards the pair of jaws when the at least one handle is spaced-apart relative to the housing, wherein at least one of the clip carrier and the shuttle box is configured to at least partially surround the distal-most clip during transport thereof from the clip carrier towards the pair of jaws.

19. The clip applier according to claim 1, further comprising a drive channel slidably supported within at least one of the housing and the channel assembly, the drive channel having a first end portion operatively connected to the at least one handle and a second end portion configured and dimensioned to selectively engage the pair of jaws to effectuate closure of the pair of jaws, the drive channel being moved towards the jaw assembly as the at least one handle is actuated in a first direction to move the second end portion thereof against the pair jaws to close the pair jaws, the drive channel being moved away from the pair jaws as the at least one handle is actuated in a second direction to move the second end portion thereof away from the pair jaws to enable the pair of jaws to open.

* * * * *